US008829047B2

(12) United States Patent
Gass et al.

(10) Patent No.: US 8,829,047 B2
(45) Date of Patent: Sep. 9, 2014

(54) METHODS OF CONTROLLING VENOUS IRRITATION ASSOCIATED WITH THE TREATMENT OF A CARDIAC DISORDER

(75) Inventors: Jerome H. Gass, Lake Villa, IL (US); Jeff McKee, McHenry, IL (US); Barrett Rabinow, Skokie, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

(21) Appl. No.: 13/358,949

(22) Filed: Jan. 26, 2012

(65) Prior Publication Data
US 2012/0277309 A1 Nov. 1, 2012

Related U.S. Application Data

(60) Provisional application No. 61/436,995, filed on Jan. 27, 2011.

(51) Int. Cl.
*A61K 31/24* (2006.01)
(52) U.S. Cl.
CPC .................................. *A61K 31/24* (2013.01)
USPC ........................ 514/534; 514/533; 514/538
(58) Field of Classification Search
USPC .......................................... 514/534, 533, 538
See application file for complete search history.

(56) References Cited

U.S. PATENT DOCUMENTS

| 4,857,552 | A | 8/1989 | Rosenberg et al. | |
|---|---|---|---|---|
| 5,017,609 | A | 5/1991 | Escobar et al. | |
| 5,849,843 | A | 12/1998 | Laurin et al. | |
| 5,977,409 | A | 11/1999 | Erhardt | |
| 5,998,019 | A | 12/1999 | Rosenbaum et al. | |
| 6,310,094 | B1 * | 10/2001 | Liu et al. | 514/538 |
| 2006/0286037 | A1 | 12/2006 | Hirano et al. | |
| 2012/0184545 | A1 | 7/2012 | Hirano et al. | |
| 2012/0302637 | A1 | 11/2012 | Rabinow et al. | |

FOREIGN PATENT DOCUMENTS

| CN | 101323580 A | 12/2008 |
|---|---|---|
| CN | 101881755 A | 11/2010 |
| CN | 101891636 A | 11/2010 |
| CN | 102106846 A | 6/2011 |
| WO | WO-85/04580 A1 | 10/1985 |
| WO | WO-87/03583 A1 | 6/1987 |
| WO | WO 8703583 A1 * | 6/1987 |
| WO | WO-88/01614 A1 | 3/1988 |
| WO | WO-89/11855 A1 | 12/1989 |
| WO | WO-02/076446 A1 | 10/2002 |
| WO | WO-2005/014042 A1 | 2/2005 |
| WO | WO-2008/153582 A1 | 12/2008 |

OTHER PUBLICATIONS

Anargan et al., Esmolol hydrochloride: an ultrashort-acting, β-adrenergic blocking agent, Clin. Pharm., 5:288-303 (1986).
Benvenuto et al., Morbidity and mortality of orthostatic hypotension: implications for management of cardiovascular disease, Am. J. Hypertens., 24(2):135-44 (2011).
Brevibloc Premixed Injection, Baxter Healthcare Corporation, 2 pages (Sep. 18, 2010).
Byrd et al., Safety and efficacy of esmolol (ASL-8052: an ultrashort-acting beta-adrenergic blocking agent) for control of ventricular rate in supraventricular tachycardias, J. Am. Coll. Cardiol., 3(2Pt. 1):394-9 (1984).
Deegan et al., β-Receptor antagonism does not fully explain esmolol-induced hypotension, Clin. Pharmacol. Ther., 56:223-8 (1994).
DeStefano et al., Autosomal dominant orthostatic hypotensive disorder maps to chromosome 18q, Am. J. Hum. Genet., 63(5):1425-30 (1998).
Esmolol Hydrochloride Injection Ready-to-Use 10 mL Vials, Packaging Insert, Baxter Healthcare Corporation (Mar. 2003).
Hartmann et al., The incidence and risk factors for hypotension after spinal anesthesia induction: an analysis with automated data collection, Anesth. Analg., 94(6):1521-9 (2002).
Hessov et al., Experimental infusion thrombophlebitis. Importance of the pH of glucose solutions, Eur. J. Intensive Care Med., 2(2):97-101 (1976).
Hoover et al., Comparison of in vitro and in vivo models to assess venous irritation of parenteral antibiotics, Fundam. Appl. Toxicol., 14(3):589-97 (1990).
International Search Report and Written Opinion from corresponding International application No. PCT/US2010/022679, mailing date Mar. 15, 2012.
Jacobs et al., Esmolol and left ventricular function in the awake dog, Anesthesiology, 68(3):373-8 (1988).
Johnson et al., Development of an in vivo model for assessment of drug-induced vascular injury, J. Oral Maxillofac. Surg., 47(8):819-22 (1989).
Ko et al., A new dosing regimen for esmolol to treat supraventricular tachyarrhythmia in Chinese patients, J. Am. Coll. Cardiol., 23(2):302-6 (1994).
Laupland, Population-based epidemiology of intensive care: critical importance of ascertainment of residency status, Critical Care, 8:R431-6 (2004).
Mehvar et al., Stereospecific pharmacokinetics and pharmacodynamics of beta-adrenergic blockers in humans, J. Pharm. Pharm. Sci., 4(2):185-200 (2001).

(Continued)

*Primary Examiner* — Kevin E Weddington
(74) *Attorney, Agent, or Firm* — Marshall, Gerstein & Borun LLP

(57) ABSTRACT

A pharmaceutical composition comprising (S)-methyl-3-[4-(2-hydroxy-3-isopropylamino)propoxy]phenylpropionate in a concentration between about 75 mM and about 150 mM, which is substantially free of the R-isomer or pharmaceutically acceptable salt thereof, is provided. A method of treating a cardiac disorder is also provided and includes administering to a subject in need thereof a therapeutically effective amount of a pharmaceutical composition comprising (S)-methyl-3-[4-(2-hydroxy-3-isopropylamino)propoxy]phenylpropionate hydrochloride, wherein the (S)-methyl-3-[4-(2-hydroxy-3-isopropylamino)propoxy]phenylpropionate hydrochloride is present at a concentration between about 75 mM and about 150 mM and wherein the pharmaceutical composition is substantially free of (R)-methyl-3-[4-(2-hydroxy-3-isopropylamino)propoxy]phenylpropionate or pharmaceutically acceptable salt thereof.

41 Claims, 6 Drawing Sheets

(56) References Cited

OTHER PUBLICATIONS

Moreno et al., Intrapericardial beta-adrenergic blockade with esmolol exerts a potent antitachycardic effect without depressing contractility, J. Cardiovasc. Pharmacol., 36(6):722-7 (2000).

Murthy et al., Cardiovascular pharmacology of ASL-8052, an ultra-short acting beta blocker, Eur. J. Pharmacol., 92(1-2):43-51 (1983).

NDA 19-386: Review and Evaluation of Pharmacology and Toxicology Data, American Critical Care, McGraw Park, Illinois (1986).

Ornstein et al., Are all effects of esmolol equally rapid in onset?, Anesth. Analg. 81:297-300 (1995).

Reich et al., Predictors of hypotension after induction of general anesthesia, Anesth. Analg., 101(3):622-8 (2005).

Reilly et al., Ultra-short-acting beta-blockade: a comparison with conventional beta-blockade, Clin. Pharmacol. Ther., 38(5):579-85 (1985).

Robertson, Genetics and molecular biology of hypotension, Curr. Opin. Nephrol. Hypertens., 3(1):13-24 (1994).

Sung et al., Clinical experience with esmolol, a short-acting beta-adrenergic blocker in cardiac arrhythmias and myocardial ischemia, J. Clin. Pharmacol., 26 (suppl A): A15-A26 (1986).

Tang et al., Stereoselective RP-HPLC determination of esmolol enantiomers in human plasma after pre-column derivatization, J. Biochem. Biophys. Methods, 59(2):159-66 (2004).

Wu et al., Population-based study on the prevalence and risk factors of orthostatic hypotension in subjects with pre-diabetes and diabetes, Diabetes Care, 32(1):69-74 (2009).

Yu et al., The safety of perioperative esmolol: a systematic review and meta-analysis of randomized controlled trials, Anesth. Analg., 112(2):267-81 (2011).

Zaugg et al., Adrenergic receptor genotype but not perioperative bisoprolol therapy may determine cardiovascular outcome in at-risk patients undergoing surgery with spinal block: the Swiss Beta Blocker in Spinal Anesthesia (BBSA) study: a double-blinded, placebo-controlled, multicenter trial with 1-year follow-up, Anesthesiology, 107(1):33-44 (2007).

Zaugg et al., Genetic modulation of adrenergic activity in the heart and vasculature: Implications for perioperative medicine, Anesthesiology, 102:429-46 (2005).

International Preliminary Report on Patentability, issued Jun. 24, 2013, in corresponding International Application No. PCT/US2012/022679.

Conolly et al., Metabolism of isoprenaline in dog and man, Br. J. Pharmacol., 46(3):458-72 (1972).

Fleischer, 2009 ACCF/AHA focused update on perioperative beta blockade incorporated into the ACC/AHA 2007 guidelines on perioperative cardiovascular evaluation and care for noncardiac surgery, J. Am. Coll. Cardiol., 54:e13-e118 (2009).

Quon et al., Pharmacodynamics and onset of action of esmolol in anesthetized dogs, J. Pharmacol. Exp. Ther., 237(3):912-8 (1986).

Shaffer et al., Beta-adrenoreceptor antagonist potency and pharmacodynamics of ASL-8123, the primary acid metabolite of esmolol, J. Cardiovasc. Pharmacol., 11(2):187-92 (1988).

\* cited by examiner

US 8,829,047 B2

METHODS OF CONTROLLING VENOUS IRRITATION ASSOCIATED WITH THE TREATMENT OF A CARDIAC DISORDER

CROSS-REFERENCE TO RELATED APPLICATION

The benefit under 35 U.S.C. §119(e) of U.S. provisional patent application Ser. No. 61/436,995 filed Jan. 27, 2011, the entire disclosure of which is incorporated herein by reference, is hereby claimed.

FIELD OF THE INVENTION

The invention relates to compositions and methods for treating a cardiac condition while minimizing venous irritation comprising administering a therapeutically effective amount of a pharmaceutical composition comprising the S-isomer of esmolol.

BACKGROUND

Esmolol hydrochloride (methyl-3-[4-(2-hydroxy-3-isopropylamino)propoxy]phenylpropionate hydrochloride) is a 50:50 racemic mixture of S- and R-isomers. Esmolol hydrochloride is a fast-onset beta-blocker used for treatment of cardiac disorders, such as tachycardia and hypertension. Most currently available beta-blockers have relatively long onset times. However, it is often desirable in the critical care setting to quickly reduce heart rate and/or improve rhythmicity during a cardiac crisis, e.g., during or shortly after a myocardial infarction. Conventional beta-blocking agents can be employed for such treatment, but their relatively long onset times can prevent a clinician from effectively titrating the dose quickly, e.g., when a patient is in crisis. Esmolol hydrochloride is particularly useful when treating a patient experiencing a cardiac crisis. Because of its relatively fast onset time, feedback is immediate and thus dosing can be adjusted quickly according to the patient's response.

Esmolol hydrochloride differs from conventional beta-blocking compounds in that it contains an ester functional group which can be rapidly hydrolyzed. Esmolol hydrochloride has a short duration in vivo due to the presence of the ester group and is indicated for the rapid control of ventricular rate in patients with supraventricular tachycardia (i.e., atrial fibrillation or atrial flutter) in perioperative, postoperative, or other emergent circumstances where short term control of ventricular rate with a short-acting agent is desirable. Esmolol hydrochloride is also indicated for intraoperative and postoperative tachycardia and/or hypertension. Esmolol hydrochloride is typically administered by infusion. A significant number of patients experience venous irritation at the infusion site. See Esmolol Hydrochloride Injection Ready-to-use 10 mL Vials, packaging insert (Baxter Healthcare Corporation). The incidence and amount of venous irritation observed in patients increases along with the concentration of the dose of esmolol hydrochloride administered. Id. Therefore, a desired higher infusion concentration often cannot be used to lower the heart rate of a patient in stress because of concern that significant venous irritation may develop. As a result, effective esmolol hydrochloride administration often takes longer than it otherwise would if higher infusion concentrations were administered.

In view of the foregoing, it would be advantageous to retain the efficacious beta-blockade effects of esmolol hydrochloride while minimizing the bothersome venous irritation that occurs with significant frequency in esmolol hydrochloride administration.

SUMMARY OF THE INVENTION

The present disclosure provides methods and compositions for treating cardiac conditions (e.g. tachycardia and hypertension) and/or controlling heart rate by administering pharmaceutical compositions comprising the S-isomer of esmolol or a pharmaceutically acceptable salt thereof in order to minimize the venous irritation often associated with administration of the racemic mixture of esmolol hydrochloride.

In one aspect, the invention provides a pharmaceutical composition comprising (S)-methyl-3-[4-(2-hydroxy-3-isopropylamino)propoxy]phenylpropionate or a pharmaceutically acceptable salt thereof, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof.

In a related aspect, the invention provides an aqueous pharmaceutical composition comprising: (S)-methyl-3-[4-(2-hydroxy-3-isopropylamino)propoxy]phenylpropionate or a pharmaceutically acceptable salt thereof, an osmotic adjusting agent, and a buffer, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof.

In yet another related aspect, the invention provides a method of treating a cardiac disorder comprising administering to a subject in need thereof a therapeutically effective amount of a pharmaceutical composition comprising (S)-methyl-3-[4-(2-hydroxy-3-isopropylamino)propoxy]phenylpropionate or a pharmaceutically acceptable salt thereof, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof.

In another aspect, the invention provides a method of controlling heart rate comprising administering to a subject in need thereof a therapeutically effective amount of a pharmaceutical composition comprising (S)-methyl-3-[4-(2-hydroxy-3-isopropylamino)propoxy]phenylpropionate or a pharmaceutically acceptable salt thereof, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof.

Other features and advantages of the present invention will become apparent from the following detailed description and claims.

DETAILED DESCRIPTION

Figure 1A:
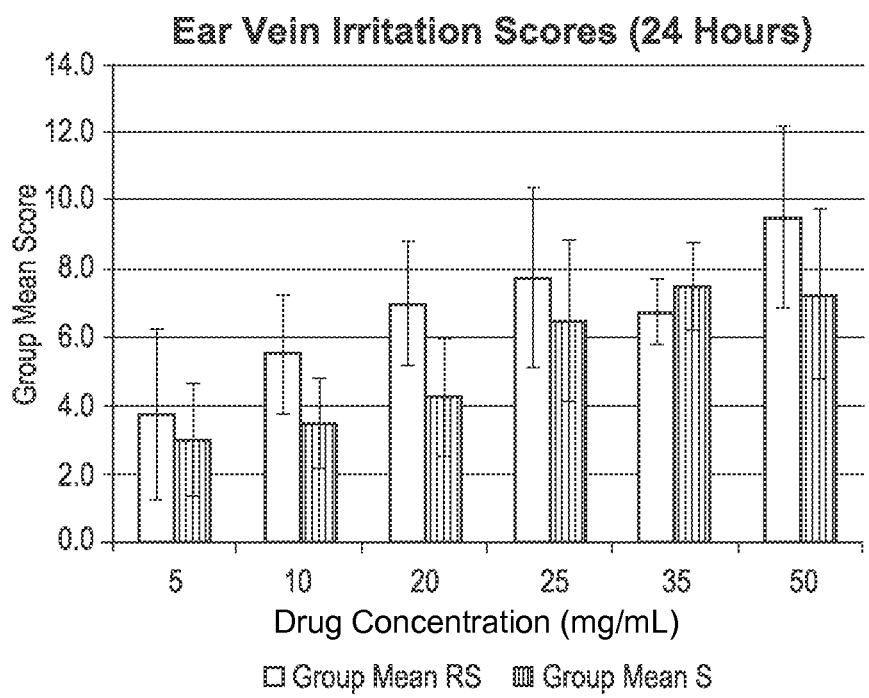
FIGS. 1A-1B illustrate the composite scores for a rabbit ear vein irritation test comparing the effects of administering a composition comprising the racemic mixture of esmolol to a composition comprising the S-isomer of esmolol at 24 hours post-infusion (FIG. 1A) and 72 hours post-infusion (FIG. 1B).

The present disclosure provides methods and compositions for treating cardiac conditions, including hypertension (e.g., intraoperative and postoperative hypertension) and tachycardia (e.g., supraventricular tachycardia, intraoperative and postoperative tachycardia) with compositions comprising the S-isomer of esmolol in order to minimize the venous irritation often associated with administration of the racemic mixture of esmolol. The present disclosure also provides methods and compositions for controlling heart rate with compositions comprising the S-isomer of esmolol in order to minimize the venous irritation sometimes associated with administration of the racemic mixture of esmolol. The inventors have made the unexpected and surprising finding that significantly less venous irritation is observed when a composition comprising (S)-methyl-3-[4-(2-hydroxy-3-isopropylamino)propoxy] phenylpropionate or pharmaceutically acceptable salt thereof is administered at a concentration between about 60 mM and about 150 mM and more preferably when the composition comprising the S-isomer of esmolol is administered at a concentration between about 75 mM and about 150 mM. Surprisingly, when the disclosed compositions comprising the S-isomer of esmolol are administered, significantly less venous irritation is observed relative to an equal concentration of the racemic mixture, and the effect of reduced venous irritation is particularly noticeable when an equitherapeutic concentration of the S-isomer of esmolol is compared to a corresponding concentration of the racemic mixture. Moreover, we have found that reduced venous irritation is (drug) concentration dependent as demonstrated herein despite the fact that the administered amount (i.e., the infusion rate) was held constant.

As explained above, esmolol is often used by practitioners for its rapid onset of action and generally requires dose titration based upon the patient body weight and response. For diabetic patients, obese patients, and fluid-restricted patients, in particular, it would be highly desirable to administer a relatively concentrated esmolol composition that can be administered without dilution or with minimal volume dilution. The invention provides such compositions and methods for administering same. For example, fluid-restricted patients, e.g., patients under fluid restriction because of congestive heart failure or other conditions sensitive to volume infusions, can benefit from the disclosed methods and compositions because higher therapeutic concentrations of the disclosed S-esmolol-containing compositions can be administered, thereby minimizing volumetric effects to such patients. Such higher drug concentrations can be administered because the venous irritation typically associated with compositions comprising the racemic mixture is lessened when the disclosed compositions comprising S-esmolol are administered. Moreover, compositions comprising the S-isomer of esmolol can contain significantly less salt than compositions comprising the racemic mixture of esmolol because higher drug concentrations can be administered (as explained above) and thus there is reduced need for salt to contribute to the osmoticity of the solution (such that it is isotonic), thereby minimizing the daily salt (i.e., sodium chloride) intake associated with the treatment, which can be particularly beneficial for patients on salt-restricted diets (e.g., patients suffering from congestive heart failure and/or high blood pressure). Similarly, compositions comprising the S-isomer of esmolol can contain significantly less dextrose than compositions comprising the racemic mixture of esmolol because higher drug concentrations can be administered (as explained above) and thus there is reduced need for dextrose to contribute to the osmoticity of the solution such that it is isotonic, thereby minimizing the simple sugar intake associated with the treatment, which can be particularly beneficial for diabetic patients.

In one aspect, the invention provides a pharmaceutical composition comprising: (S)-methyl-3-[4-(2-hydroxy-3-isopropylamino)propoxy]phenylpropionate (S-esmolol) or a pharmaceutically acceptable salt thereof, wherein the (S)-methyl-3-[4-(2-hydroxy-3-isopropylamino)propoxy]phenylpropionate hydrochloride is present at a concentration between about 60 mM and about 150 mM, and wherein the pharmaceutical composition is substantially free of (R)-methyl-3-[4-(2-hydroxy-3-isopropylamino)propoxy]phenylpropionate hydrochloride or pharmaceutically acceptable salt thereof.

In a related aspect, the invention provides an aqueous pharmaceutical composition comprising: (S)-methyl-3-[4-(2-hydroxy-3-isopropylamino)propoxy]phenylpropionate (S-esmolol) or a pharmaceutically acceptable salt thereof, an osmotic adjusting agent, and a buffer, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof.

In yet another related aspect, the invention provides a method of treating a cardiac disorder comprising administering to a subject in need thereof a therapeutically effective amount of a pharmaceutical composition comprising (S)-methyl-3-[4-(2-hydroxy-3-isopropylamino)propoxy]phenylpropionate (S-esmolol) or a pharmaceutically acceptable salt thereof, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof. In various embodiments according to this aspect, the pharmaceutical composition comprises (S)-methyl-3-[4-(2-hydroxy-3-isopropylamino)propoxy]phenylpropionate or a pharmaceutically acceptable salt thereof at a concentration between about 75 mM and about 150 mM, between about 75 mM and about 135 mM, between about 90 mM and about 150 mM, between about 90 mM and about 135 mM, between about 105 mM and about 150 mM, and/or between about 105 mM and about 135 mM. In all embodiments of this aspect, the pharmaceutical composition can comprise (S)-methyl-3-[4-(2-hydroxy-3-isopropylamino)propoxy]phenylpropionate hydrochloride at a concentration between about 20 mg/mL and about 50 mg/mL, between about 25 mg/mL and about 50 mg/mL, between about 25 mg/mL and about 45 mg/mL, between about 30 mg/mL and about 50 mg/mL, between about 30 mg/mL and about 45 mg/mL, between about 35 mg/mL and/or about 45 mg/mL.

In another related aspect, the invention provides a method of controlling heart rate comprising administering to a subject in need thereof a therapeutically effective amount of a pharmaceutical composition comprising (S)-methyl-3-[4-(2-hydroxy-3-isopropylamino)propoxy]phenylpropionate or a pharmaceutically acceptable salt thereof, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof.

In yet another related aspect, the invention provides a method of treating a cardiac disorder comprising administering to a subject in need thereof a therapeutically effective amount of a pharmaceutical composition comprising (S)-methyl-3-[4-(2-hydroxy-3-isopropylamino)propoxy]phenylpropionate (S-esmolol) or a pharmaceutically acceptable salt thereof, wherein the (S)-methyl-3-[4-(2-hydroxy-3-isopropylamino)propoxy]phenylpropionate or pharmaceutically acceptable salt thereof is present at a concentration between about 3 mM and about 300 mM, and wherein the pharmaceutical composition is substantially free of (R)-methyl-3-[4-(2-hydroxy-3-isopropylamino)propoxy]phenylpropionate or pharmaceutically acceptable salt thereof. Patients treated according to this aspect of the invention are in need of beta blockade and are susceptible to venous irritation, for example, because they are already taking drugs that are veno-irritative (e.g., amiodarone, intravenous antibiotics, kidney patients being hemodialyzed), they suffer from an inflammatory condition that causes venous irritation such as systemic lupus erythematosus or venous thrombosis, are of advanced age, are diabetic, are obese, and/or are a drug abuser. According to this method, the (S)-methyl-3-[4-(2-hydroxy-3-isopropylamino)propoxy]phenylpropionate (S-esmolol) or pharmaceutically acceptable salt thereof is present at a concentration between about 3 mM and about 300 mM, between about 15 mM and about 300 mM, between about 30 mM and about 300 mM, between about 45 mM and about 300 mM, between about 60 mM and about 300 mM, between about 75 mM and about 300 mM, between about 90 mM and about 300 mM, between about 105 mM and about 300 mM, between about 120 mM and about 300 mM, between about 135 mM and about 300 mM, between about 150 mM and about 300 mM, between about 165 mM and about 300 mM, between about 180 mM and about 300 mM, between about 195 mM and about 300 mM, between about 210 mM and about 300 mM, and/or between about 225 mM and about 300 mM. In all disclosed embodiments of the foregoing method, the pharmaceutical composition can comprise (S)-methyl-3-[4-(2-hydroxy-3-isopropylamino)propoxy]phenylpropionate hydrochloride (S-esmolol hydrochloride) at a concentration between about 1 mg/mL and about 100 mg/mL, between about 5 mg/mL and about 100 mg/mL, between about 10 mg/mL and about 100 mg/mL, between about 15 mg/mL and about 100 mg/mL, between about 20 mg/mL and about 100 mg/mL, between about 25 mg/mL and about 100 mg/mL, between about 30 mg/mL and about 100 mg/mL, between about 35 mg/mL and about 100 mg/mL, between about 40 mg/mL and about 100 mg/mL, between about 45 mg/mL and about 100 mg/mL, between about 50 mg/mL and about 100 mg/mL, between about 55 mg/mL and about 100 mg/mL, between about 60 mg/mL and about 100 mg/mL, between about 65 mg/mL and about 100 mg/mL, between about 70 mg/mL and about 100 mg/mL, and/or between about 75 mg/mL and about 100 mg/mL.

In yet an additional related aspect, the invention provides a method of controlling heart rate comprising administering to a subject in need thereof a therapeutically effective amount of a pharmaceutical composition comprising (S)-methyl-3-[4-(2-hydroxy-3-isopropylamino)propoxy]phenylpropionate (S-esmolol) or a pharmaceutically acceptable salt thereof, wherein the (S)-methyl-3-[4-(2-hydroxy-3-isopropylamino)propoxy]phenylpropionate or pharmaceutically acceptable salt thereof is present at a concentration between about 3 mM and about 300 mM, and wherein the pharmaceutical composition is substantially free of (R)-methyl-3-[4-(2-hydroxy-3-isopropylamino)propoxy]phenylpropionate or pharmaceutically acceptable salt thereof. Patients treated according to this aspect of the invention are in need of beta blockade and are susceptible to venous irritation, for example, because they are already taking drugs that are veno-irritative (e.g., amiodarone, intravenous antibiotics, kidney patients being hemodialyzed), they suffer from an inflammatory condition that causes venous irritation such as systemic lupus erythematosus or venous thrombosis, are of advanced age, are diabetic, are obese, and/or are a drug abuser. According to this method, the (S)-methyl-3-[4-(2-hydroxy-3-isopropylamino)propoxy]phenylpropionate (S-esmolol) or pharmaceutically acceptable salt thereof is present at a concentration between about 3 mM and about 300 mM, between about 15 mM and about 300 mM, between about 30 mM and about 300 mM, between about 45 mM and about 300 mM, between about 60 mM and about 300 mM, between about 75 mM and about 300 mM, between about 90 mM and about 300 mM, between about 105 mM and about 300 mM, between about 120 mM and about 300 mM, between about 135 mM and about 300 mM, between about 150 mM and about 300 mM, between about 165 mM and about 300 mM, between about 180 mM and about 300 mM, between about 195 mM and about 300 mM, between about 210 mM and about 300 mM, and/or between about 225 mM and about 300 mM. In all disclosed embodiments of the foregoing method, the pharmaceutical composition can comprise (S)-methyl-3-[4-(2-hydroxy-3-isopropylamino)propoxy]phenylpropionate hydrochloride (S-esmolol hydrochloride) at a concentration between about 1 mg/mL and about 100 mg/mL, between about 5 mg/mL and about 100 mg/mL, between about 10 mg/mL and about 100 mg/mL, between about 15 mg/mL and about 100 mg/mL, between about 20 mg/mL and about 100 mg/mL, between about 25 mg/mL and about 100 mg/mL, between about 30 mg/mL and about 100 mg/mL, between about 35 mg/mL and about 100 mg/mL, between about 40 mg/mL and about 100 mg/mL, between about 45 mg/mL and about 100 mg/mL, between about 50 mg/mL and about 100 mg/mL, between about 55 mg/mL and about 100 mg/mL, between about 60 mg/mL and about 100 mg/mL, between about 65 mg/mL and about 100 mg/mL, between about 70 mg/mL and about 100 mg/mL, and/or between about 75 mg/mL and about 100 mg/mL.

The cardiac conditions and/or disorders which can be treated by the methods of the invention include any cardiac condition known to benefit from treatment with esmolol. Such cardiac conditions include, but are not limited to, tachycardias, including supraventricular tachycardias, intraoperative tachycardias, and postoperative tachycardias, and hypertension, including intraoperative hypertension and postoperative hypertension. Moreover, the methods of the invention can also be used to control heart rate in a patient, when clinically desirable, whether or not the subject has one of the aforementioned cardiac conditions.

As used herein the terms "pharmaceutical composition comprising (S)-methyl-3-[4-(2-hydroxy-3-isopropylamino)propoxy]phenylpropionate or a pharmaceutically acceptable salt thereof," and "composition comprising the S-isomer of esmolol" refer to pharmaceutical compositions which are substantially free of (R)-methyl-3-[4-(2-hydroxy-3-isopropylamino)propoxy]phenylpropionate or a pharmaceutically acceptable salt thereof. The term "substantially free of (R)-methyl-3-[4-(2-hydroxy-3-isopropylamino)propoxy]phenylpropionate" refers to compositions that contain less than 10% by weight, less than 5% by weight, less than 3% by weight, less than 2% by weight, less than 1% by weight, and/or less than 0.5% by weight (R)-methyl-3-[4-(2-hydroxy-3-isopropylamino)propoxy]phenylpropionate or a pharmaceutically acceptable salt thereof based on the total amount of methyl-3-[4-(2-hydroxy-3-isopropylamino)propoxy]phenylpropionate or pharmaceutically acceptable salt thereof in the composition. Preferably, "substantially free of (R)-methyl-3-[4-(2-hydroxy-3-isopropylamino)propoxy] phenylpropionate" refers to compositions that contain 5 wt. % or less of (R)-methyl-3-[4-(2-hydroxy-3-isopropylamino) propoxy]phenylpropionate or a pharmaceutically acceptable salt thereof based on the total amount of methyl-3-[4-(2-hydroxy-3-isopropylamino)propoxy]phenylpropionate or pharmaceutically acceptable salt thereof in the composition, e.g., less than 3 wt. %, less than 2 wt. %, less than 1 wt. %, and/or less than 0.5 wt. %. The total esmolol content can be determined using a standard HPLC column or similar analytical method known in the art. The respective relative contents of the S-isomer of esmolol and the R-isomer of esmolol in a given composition can be determined using a chiral HPLC method or similar analytical method known in the art. See, e.g., Tang et al., *J. Biochem. Biophys. Methods,* 59:159-166 (2004).

In one aspect, a "therapeutically effective amount" refers to an amount of a pharmaceutical composition comprising (S)-methyl-3-[4-(2-hydroxy-3-isopropylamino)propoxy]phenylpropionate or a pharmaceutically acceptable salt thereof which is sufficient to control tachycardia and/or hypertension. Thus, an amount sufficient to control tachycardia includes but is not limited to an amount sufficient to alleviate and/or ameliorate tachycardia and/or hypertension.

In another aspect, a "therapeutically effective amount" refers to an amount of a pharmaceutical composition comprising (S)-methyl-3-[4-(2-hydroxy-3-isopropylamino)propoxy]phenylpropionate or a pharmaceutically acceptable salt thereof which is sufficient to control heart rate. Thus, an amount sufficient to control heart rate includes but is not limited to an amount sufficient to control and/or reduce an elevated heart rate.

The term "pharmaceutically acceptable salt" refers to those salts which retain the biological efficacy and properties of the esmolol, and which are not biologically or otherwise undesirable. Such salts can be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In all disclosed embodiments, the pharmaceutically acceptable salt of (S)-methyl-3-[4-(2-hydroxy-3-isopropylamino)propoxy]phenylpropionate can be (S)-methyl-3-[4-(2-hydroxy-3-isopropylamino) propoxy]phenylpropionate hydrochloride.

As used herein, the term a "subject in need thereof" (i.e., in need of tachycardia and/or hypertension treatment) is defined as an individual who would benefit from administration of a beta blocker to control tachycardia and/or hypertension. In particular, the term refers to an individual who would benefit from administration of a beta blocker to control tachycardia and/or hypertension and is susceptible to the development of venous irritation relative to administration of an equal concentration of the racemic mixture (and even moreso when a concentration of the racemic mixture is administered that corresponds to an equitherapeutic concentration of the S-isomer of esmolol).

In another aspect, the term a "subject in need thereof" (i.e., in need of heart rate control) is defined as an individual who would benefit from administration of a beta blocker to control an elevated heart rate. In particular, the term refers to an individual who would benefit from administration of a beta blocker to control an elevated heart rate and is susceptible to the development of venous irritation relative to administration of an equal concentration of a pharmaceutical composition comprising the racemic mixture (and even moreso when a concentration of the racemic mixture is administered that corresponds to an equitherapeutic concentration of the S-isomer of esmolol).

As used herein, the term "tachycardia" refers to an abnormally fast heart beat, typically for humans age 15 or older, a heart rate greater than 100 beats per minute at rest. "Supraventricular tachycardia" refers to such an abnormally fast heart beat originating in the atria.

As used herein, the term "hypertension" refers to abnormally high blood pressure. As appreciated by those of skill in the art, blood pressure characterized as "hypertensive" may vary from individual to individual. Hypertension, however, is generally defined as systolic pressure greater than 140 mmHg and/or diastolic pressure greater than 90 mmHg.

As used herein, the term "elevated heart rate" refers to a heart rate that is more than 20 beats per minute higher than an individual's normal resting pulse, more typically more than 25 beats per minute higher than the individual's normal resting pulse, and/or more than 30 beats per minute higher than the individual's normal resting pulse. Such elevated heart rates may not be tachycardias as defined herein, but tachycardias are also encompassed by the foregoing definition of elevated heart rate.

The claimed pharmaceutical compositions generally comprise (S)-methyl-3-[4-(2-hydroxy-3-isopropylamino)propoxy]phenylpropionate or a pharmaceutically acceptable salt thereof at a concentration between about 60 mM and about 150 mM and more preferably between about 75 mM and about 150 mM. In various embodiments, the pharmaceutical composition comprises (S)-methyl-3-[4-(2-hydroxy-3-isopropylamino)propoxy]phenylpropionate or a pharmaceutically acceptable salt thereof at a concentration between about 75 mM and about 135 mM, about 90 mM and about 150 mM, between about 90 mM and about 135 mM, between about 105 mM and about 150 mM, and/or between about 105 mM and about 135 mM. In all embodiments of the claimed composition, the pharmaceutical composition can comprise (S)-methyl-3-[4-(2-hydroxy-3-isopropylamino)propoxy]phenylpropionate hydrochloride at a concentration between about 20 mg/mL and about 50 mg/mL, between about 25 mg/mL and about 50 mg/mL, between about 25 mg/mL and about 45 mg/mL, between about 30 mg/mL and about 50 mg/mL, between about 30 mg/mL and about 45 mg/mL, and/or between about 35 mg/mL and about 45 mg/mL. In related embodiments, the pharmaceutical composition comprising (S)-methyl-3-[4-(2-hydroxy-3-isopropylamino)propoxy]phenylpropionate or a pharmaceutically acceptable salt thereof can be substantially free of propylene glycol and ethanol.

While beta blockers are typically manufactured and commercialized as the RS racemic mixture, the S-isomer is responsible for all of the beta blocking activity. See Mehvar and Brocks, *J. Pharm. Pharmaceut. Sci.*, 4(2):185-200 (2001). Consistent with the foregoing, International Patent Publication No. WO 88/01614 discloses that the S-isomer of esmolol is about twice as potent as a beta-adrenergic-blocking agent than an equivalent amount of the racemic mixture. Thus, as used herein, the term "equitherapeutic concentration" refers to a concentration of (S)-methyl-3-[4-(2-hydroxy-3-isopropylamino)propoxy]phenylpropionate or a pharmaceutically acceptable salt thereof that provides the same therapeutic beta-blockade benefit as a given concentration of a racemic mixture of methyl-3-[4-(2-hydroxy-3-isopropylamino)propoxy]phenylpropionate or a pharmaceutically acceptable salt thereof. In general, an equitherapeutic concentration of (S)-methyl-3-[4-(2-hydroxy-3-isopropylamino)propoxy]phenylpropionate or a pharmaceutically acceptable salt thereof is one-half the concentration of the racemic mixture of methyl-3-[4-(2-hydroxy-3-isopropylamino)propoxy]phenylpropionate or a pharmaceutically acceptable salt thereof. In other words, if the amount of drug in the composition comprising the racemic mixture of esmolol is 50 mg/mL, the equitherapeutic concentration of the S-isomer of esmolol is 25 mg/mL.

The pharmaceutical composition of the present invention is suitable for parenteral administration to a patient. Suitable routes for parenteral administration include subcutaneous, intradermal, intramuscular, intraarticular, and intrathecal. For example, the pharmaceutical composition comprising (S)-methyl-3-[4-(2-hydroxy-3-isopropylamino)propoxy]phenylpropionate or a pharmaceutically acceptable salt thereof may be administered in the form of a bolus injection, intravenous infusion, or combination bolus injection/intravenous infusion. The ready-to-use formulation of the invention is preferably administered by intravenous infusion.

The pharmaceutical composition comprising (S)-methyl-3-[4-(2-hydroxy-3-isopropylamino)propoxy]phenylpropionate or pharmaceutically acceptable salt thereof takes the form of a sterile, ready-to-use formulation suitable for infusion. The ready-to-use presentation avoids the inconvenience of diluting a concentrated small volume parenteral formulation into infusion diluents prior to infusion, as well as eliminates the risk of microbiological contamination during handling and any potential calculation or dilution error. As used herein, a "ready-to-use" formulation or composition is defined as a composition comprising (S)-methyl-3-[4-(2-hydroxy-3-isopropylamino)propoxy]phenylpropionate or pharmaceutically acceptable salt thereof that does not need dilution before administration to the patient. Similarly, "suitable for parental infusion" refers to formulations or compositions wherein the pH and osmolarity have been adjusted to physiological or near-physiological levels appropriate for administration to the patient by infusion. Such formulations can be essentially free from propylene glycol and ethanol.

When treating tachycardias, the administered dose of the composition comprising the S-isomer of esmolol or pharmaceutically acceptable salt thereof is typically titrated using the ventricular rate as a guide. Generally, the administered dose of the S-isomer of esmolol hydrochloride is between 12.5 µg/kg/minute and 1000 µg/kg/minute, between 12.5 µg/kg/minute and 500 µg/kg/minute, between 12.5 µg/kg/minute and 400 µg/kg/minute, between 12.5 µg/kg/minute and 300 µg/kg/minute, between 12.5 µg/kg/minute and 200 µg/kg/minute, and/or between 12.5 µg/kg/minute and 100 µg/kg/minute. For example, a representative dosing protocol for treating supraventricular tachycardia may include an initial loading dose of 250 µg S-isomer esmolol hydrochloride/kg body weight (µg/kg) infused over a minute duration followed by a maintenance infusion of 25 µg/kg/minute S-isomer of esmolol hydrochloride for 4 minutes to obtain a guide with respect to the responsiveness of ventricular rate. A lower initial maintenance dose of S-isomer of esmolol hydrochloride such as, for example, 12.5 µg/kg/minute, or a higher initial maintenance dose of S-isomer of esmolol hydrochloride such as, for example, 37.5 µg/kg/minute, 50 µg/kg/minute, 62.5 µg/kg/minute, 75 µg/kg/minute, 87.5 µg/kg/minute, or even 100 µg/kg/minute may be used. In the dose calculations for the compositions comprising the S-isomer of esmolol according to the invention, it is assumed that the administered esmolol comprises 100% S-isomer. In some instances, after the 4 minutes of initial maintenance infusion, and depending on whether the desired ventricular response has been achieved, the loading dose of 250 µg/kg S-isomer of esmolol hydrochloride infused over a 1 minute period is repeated, followed by an additional maintenance infusion which may be continued at 25 µg/kg/minute or increased step-wise to 50 µg/kg/minute for 4 more minutes. If an adequate therapeutic effect is not observed at this point, a third loading dose of 250 µg/kg S-isomer of esmolol hydrochloride may be repeated over 1 minute and followed with an additional maintenance infusion of S-isomer of esmolol hydrochloride which may be continued at the original 25 µg/kg/minute or increased to either 50 µg/kg/minute or 75 µg/kg/minute for 4 minutes. Maintenance infusions may then be continued for up to 48 hours at up to 100 µg/kg/minute to achieve the desired therapeutic effect. After achieving an adequate control of the heart rate and a stable clinical status in patients with supraventricular tachycardia, transition to alternative antiarrhythmic agents such as propranolol, digoxin, or verapamil, may be accomplished. The loading dose of the pharmaceutical composition comprising the S-isomer of esmolol can be greater than or equal to 300 µg/kg/min, greater than or equal to 350 µg/kg/min, greater than or equal to 400 µg/kg/min, greater than or equal to 450 µg/kg/min, greater than or equal to 500 µg/kg/min, greater than or equal to 550 µg/kg/min, greater than or equal to 600 µg/kg/min, greater than or equal to 650 µg/kg/min, greater than or equal to 700 µg/kg/min, greater than or equal to 750 µg/kg/min, greater than or equal to 800 µg/kg/min, greater than or equal to 850 µg/kg/min, greater than or equal to 900 µg/kg/min, greater than or equal to 950 µg/kg/min, and/or greater than or equal to 1000 µg/kg/min. If a pharmaceutically acceptable salt of S-esmolol other than the hydrochloride salt is administered, the molar equivalent to the above ranges can be administered.

When immediate response/control is desired in a clinical situation, for example, when treating acute intraoperative tachycardia and/or acute intraoperative hypertension, a bolus dose of approximately 500 µg/kg S-isomer of esmolol hydrochloride is administered over 30 seconds, followed by infusion of 75 µg/kg/min of S-isomer of esmolol hydrochloride, if necessary. The infusion rate can be adjusted up to 150 µg/kg/min S-isomer of esmolol hydrochloride to maintain (or achieve) to reach the desired heart rate and/or blood pressure, as necessary. Again, if a pharmaceutically acceptable salt of S-esmolol other than the hydrochloride salt is administered, the molar equivalent to the above ranges can be administered.

On the other hand, when gradual response/control is acceptable, for example, when treating postoperative tachycardia and/or postoperative hypertension, the representative dosing protocol for treating supraventricular tachycardia may be used. Additionally, the representative dosing protocol for treating supraventricular tachycardia may also be used by clinicians to successfully control the heart rates of patients having elevated heart rates (i.e., elevated relative to the patient's normal resting pulse, as previously described).

It will be appreciated that the treatment methods of the invention are useful in the fields of human medicine and veterinary medicine. Thus, the subject or individual to be treated may be an animal, for example, a mammal, preferably human.

Containers suitable for packaging the pharmaceutical composition comprising (S)-methyl-3-[4-(2-hydroxy-3-isopropylamino)propoxy]phenylpropionate or pharmaceutically acceptable salt thereof according to the present invention include numerous sealed containers known in the art including, but not limited to, vials, syringes, bags, bottles, and ampul presentations. Containers may be fabricated from glass or from polymeric materials. Ready-to-use formulations are typically packaged in vials, syringes, bags and bottles, while concentrated formulations are typically packaged in ampuls.

Pharmaceutical compositions according to the present invention can be prepared into small volume parenteral (SVP) and large volume parenteral (LVP) dosage forms. The dosage forms can be packaged in any suitable container. Suitable containers include, for example, glass vials, polymeric vials, ampuls, syringes, and bags with sizes ranging from 1 mL to 500 mL. SVP ready-to-use solutions are typically filled into ampules and vials in 1-100 mL presentations. In addition, syringes can be used as the container for a SVP, which are sold as "pre-filled syringes." The LVP presentations can be contained in bags or bottles. A preferred presentation for ready-to-use LVP is a polymeric bag.

Polymeric containers, such as polymeric bags, are preferably flexible and can contain or be free of polyvinylchloride (PVC). Preferred containers are free of PVC, such as those disclosed in U.S. Pat. Nos. 5,849,843 and 5,998,019. Polymeric containers can further be provided with a moisture barrier as a secondary packaging system to prevent the loss of water during storage and to further ensure the stability of the formulation. A preferred moisture barrier is an aluminum overpouch.

The pH of the pharmaceutical composition can affect the stability of the (S)-methyl-3-[4-(2-hydroxy-3-isopropylamino)propoxy]phenylpropionate or pharmaceutically acceptable salt thereof. The pH should be between 3.5 and 6.5, preferably between 4.5 and 5.5, more preferably about 5.0. The pH can be adjusted as known in the art, for example, by addition of sodium hydroxide or hydrochloric acid.

A particularly beneficial formulation contains 60-150 mM and more preferably 75-150 mM of (S)-methyl-3-[4-(2-hydroxy-3-isopropylamino)propoxy]phenylpropionate or pharmaceutically acceptable salt thereof (e.g., 20-50 mg/mL and more preferably 25-50 mg/mL S-isomer esmolol hydrochloride). Formulations containing 60-150 mM and more preferably 75-150 mM of (S)-methyl-3-[4-(2-hydroxy-3-isopropylamino)propoxy]phenylpropionate or a pharmaceutically acceptable salt thereof have been demonstrated to cause significantly less venous irritation relative to an equal concentration of the racemic mixture.

Suitable buffering agents are known in the art, and are typically present in the pharmaceutical compositions according to the invention in a concentration ranging from 0.01-2 M. Ready-to-use formulations typically have buffering agent concentrations of 0.01-0.5 M, for example, 0.02-0.1 M. Concentrated formulations typically have buffering agent concentrations of 0.5-2 M. Exemplary buffering agents include, but are not limited to, acetate, glutamate, citrate, tartrate, benzoate, lactate, gluconate, phosphate and glycine. A preferred buffering agent comprises a combination of sodium acetate and glacial acetic acid.

The pharmaceutical compositions of the invention typically are aqueous. Such aqueous pharmaceutical compositions may further comprise a pharmaceutically acceptable co-solvent to assist in solubilization of the S-isomer of esmolol or pharmaceutically acceptable salt thereof. Alternatively, the pharmaceutical compositions of the invention may be solvent-based comprising one or more pharmaceutically acceptable solvents. Examples of pharmaceutically acceptable solvents (and co-solvents) include but are not limited to ethanol, isopropanol, ethyl acetate, acetic acid, and ethanolamine.

Suitable osmotic-adjusting agents are known in the art, and are typically present in the pharmaceutical compositions according to the invention in an amount ranging from 1-500 mg/mL. Exemplary osmotic-adjusting agents include, but are not limited to, sodium chloride, dextrose, sodium bicarbonate, calcium chloride, potassium chloride, sodium lactate, Ringer's solution and lactated Ringer's solution. Preferred osmotic adjusting agents include sodium chloride and/or dextrose. In all embodiments, the disclosed formulations may contain 1-100 mg/mL osmotic-adjusting agent, for example, 3-60 mg/mL sodium chloride or 3-10 mg/mL sodium chloride.

Procedures for filling pharmaceutical compositions of the present invention in containers, and their subsequent processing are known in the art. These procedures are conventionally used to produce sterile pharmaceutical drug products often required for health care. Such processing techniques preferably use a sterilization process to destroy or eliminate any microorganisms that may be present in the pharmaceutical composition comprising (S)-methyl-3-[4-(2-hydroxy-3-isopropylamino)propoxy]phenylpropionate or pharmaceutically acceptable salt thereof following preparation and/or packaging of the pharmaceutical compositions. For example, terminal sterilization can be used to destroy all viable microorganisms within the final, sealed package containing the pharmaceutical composition. An autoclave is commonly used to accomplish terminal heat-sterilization of drug products in their final packaging.

Typical autoclave cycles in the pharmaceutical industry to achieve terminal sterilization of the final product are 121° C. for 15 minutes. The esmolol hydrochloride composition of the present invention can be autoclaved at a temperature ranging from 115° C. to 130° C. for a period of time ranging from 5 to 40 minutes without causing substantial degradation of the (S)-methyl-3-[4-(2-hydroxy-3-isopropylamino)propoxy] phenylpropionate or pharmaceutically acceptable salt thereof. Autoclaving is preferably carried out in the temperature range of 119° C. to 122° C. for a period of time ranging from 10 to 36 minutes.

Alternatively, sterile pharmaceutical compositions according to the present invention may be prepared using aseptic processing techniques. Aseptic filling is ordinarily used to prepare drug products that will not withstand heat sterilization, but in which all of the ingredients are sterile. Sterility is maintained by using sterile materials and a controlled working environment. All containers and apparatus are sterilized, preferably by heat sterilization, prior to filling. The container (e.g., vial, ampul, bag, bottle, or syringe) are then filled under aseptic conditions.

In the disclosed methods, patients treated using the compositions of the invention are in need of beta blockade and can be susceptible to venous irritation or have a history of venous irritation after receiving a composition comprising the racemic mixture of esmolol. On the other hand, patients can be susceptible to venous irritation simply because they require a relatively high therapeutic concentration to resolve their symptoms of tachycardia and/or hypertension. Additionally, patients can be susceptible to venous irritation because they are already taking drugs that are veno-irritative (e.g., amiodarone, intravenous antibiotics, kidney patients being hemodialyzed), they suffer from an inflammatory condition that causes venous irritation such as systemic lupus erythematosus or venous thrombosis, are of advanced age, are diabetic, are obese, and/or are a drug abuser.

For example, the patient to be treated can be in need of beta blockade and be suffering from an inflammatory condition such as systemic lupus erythematosus or venous thrombosis. In systemic lupus erythematosus, the immune response can cause chronic inflammation of veins, which can cause venous irritation. In venous thrombosis, clots can form which can block blood flow and cause venous irritation. Thus, in some embodiments, the patient to be treated according to the methods of the invention is in need of beta blockade and suffers from an inflammatory condition such as systemic lupus erythematosus or venous thrombosis.

Additionally, patients of advanced age are known to be susceptible to venous irritation. Thus, in various embodiments, the patients in need of treatment are in need of beta blockade and are age 65 or older.

Moreover, diabetic patients have compromised would healing ability and thus a veno-irritative insult is more serious. As a result, diabetic patients demonstrate susceptibility to venous irritation. Thus, in some embodiments, the patient to be treated according to the methods of the invention is in need of beta blockade and is diabetic.

Additionally, obese individuals are known to be more susceptible to inflammatory insult because of their relatively greater inflammatory cytokine profile. Thus, in some embodiments, the patient to be treated according to the methods of the invention is in need of beta blockade and is obese.

Moreover, intravenous drug abusers often have substantially damaged veins due to chronic puncturing of veins. Consequently, intravenous drug abuse can cause susceptibility to venous irritation. Thus, in some embodiments, the patient to be treated according to the methods of the invention is in need of beta blockade and is an intravenous drug abuser.

Patients can also be susceptible to venous irritation simply because they require a relatively high therapeutic concentration to resolve their symptoms of tachycardia and/or hypertension. For example, fluid-restricted patients, e.g., patients under fluid restriction because of congestive heart failure or other conditions sensitive to volume infusions, who are in need of beta blockade can benefit from the disclosed methods and compositions because higher therapeutic concentrations of the disclosed S-esmolol-containing compositions can be administered, thereby minimizing volumetric effects to such patients while concurrently minimizing the venous irritation often associated with administration of the racemic mixture of esmolol.

Additionally, patients experiencing severe tachyarrhythmia are in need of fast titration of high concentrations of a beta blocker, such as esmolol, in order to bring the tachyarrhythmia under control in a more rapid manner and therefore may be susceptible to significant venous irritation. Thus, in some embodiments, the patients to be treated according to the methods of the invention are in need of fast titration of high concentration of S-esmolol to control severe tachyarrhythmia.

Further, patients on salt-restricted diets who are in need of beta blockade can benefit from the disclosed methods and compositions because the disclosed compositions comprising the S-isomer of esmolol can contain significantly less salt than compositions comprising the racemic mixture of esmolol in view of the ability to administer higher drug concentrations while minimizing venous irritation. Thus, in some embodiments, the patient to be treated according to the methods of the invention is in need of beta blockade and is on a salt-restricted diet.

EXAMPLES

The following examples are provided for illustration and are not in any way to limit the scope of the invention.

Table 1 lists properties of the esmolol composition utilized in the following studies. "Batch number" refers to the intended concentration of esmolol hydrochloride. "Actual Esmolol concentration" refers to the actual concentration of esmolol hydrochloride in each particular formulation as determined by non-chiral HPLC method at the time the formulation was prepared ("pre-animal testing") or after animal testing ("post-animal testing") as indicated below. A chiral HPLC method was used to determine the ratio of S-isomer to R-isomer in the compositions. The actual esmolol concentrations determined pre-animal testing were used to determine animal dosing. The small concentration variance between pre-animal testing and post-animal testing values demonstrates the stability of the compositions. Osmolality and pH were determined post-animal testing.

TABLE 1

Compositions

| Batch number | Isomer | Actual Esmolol concentration (pre-animal testing) | Actual Esmolol concentration (post-animal testing) | Ratio S-isomer:R-isomer | Sodium Chloride | Sodium Acetate | Acetic Acid | Testing pH | Osmolality (mOsm/kg) |
|---|---|---|---|---|---|---|---|---|---|
| 5 mg/mL | S-Isomer | 4.819 mg/mL | 4.705 mg/mL | 99.4:0.6 | 6.8 mg/mL | 2.8 mg/mL | 0.546 mg/mL | 4.92 | 294 |
| 5 mg/mL | Racemate | 4.917 mg/mL | 4.896 mg/mL | 50:50 | 6.8 mg/mL | 2.8 mg/mL | 0.546 mg/mL | 4.92 | 290 |
| 10 mg/mL | S-Isomer | 9.617 mg/mL | 9.595 mg/mL | 99.4:0.6 | 5.9 mg/mL | 2.8 mg/mL | 0.546 mg/mL | 4.91 | 299 |
| 10 mg/mL | Racemate | 9.857 mg/mL | 9.888 mg/mL | 50:50 | 5.9 mg/mL | 2.8 mg/mL | 0.546 mg/mL | 4.90 | 292 |
| 20 mg/mL | S-Isomer | 19.637 mg/mL | 19.565 mg/mL | 99.4:0.6 | 4.1 mg/mL | 2.8 mg/mL | 0.546 mg/mL | 4.86 | 315 |
| 20 mg/mL | Racemate | 20.047 mg/mL | 19.904 mg/mL | 50:50 | 4.1 mg/mL | 2.8 mg/mL | 0.546 mg/mL | 4.86 | 296 |
| 25 mg/mL | S-Isomer | 24.299 mg/mL | 24.275 mg/mL | 99.4:0.6 | 3.2 mg/mL | 2.8 mg/mL | 0.546 mg/mL | 4.86 | 313 |
| 25 mg/mL | Racemate | 25.319 mg/mL | 25.114 mg/mL | 50:50 | 3.2 mg/mL | 2.8 mg/mL | 0.546 mg/mL | 4.84 | 297 |
| 35 mg/mL | S-Isomer | 33.955 mg/mL | 34.514 mg/mL | 99.4:0.6 | 1.3 mg/mL | 2.8 mg/mL | 0.546 mg/mL | 4.81 | 321 |
| 35 mg/mL | Racemate | 35.187 mg/mL | 34.975 mg/mL | 50:50 | 1.3 mg/mL | 2.8 mg/mL | 0.546 mg/mL | 4.79 | 292 |
| 50 mg/mL | S-Isomer | 49.000 mg/mL | 48.671 mg/mL | 99.4:0.6 | 0.0 mg/mL | 2.8 mg/mL | 0.546 mg/mL | 4.75 | 372 |
| 50 mg/mL | Racemate | 50.377 mg/mL | 50.510 mg/mL | 50:50 | 0.0 mg/mL | 2.8 mg/mL | 0.546 mg/mL | 4.75 | 322 |

Example 1

A rabbit ear vein irritation test was used to assess the relative potential of (i) a composition comprising the racemic mixture of methyl-3-[4-(2-hydroxy-3-isopropylamino)propoxy]phenylpropionate hydrochloride ("Racemate" in Table 1) and (ii) a composition comprising (S)-methyl-3-[4-(2-hydroxy-3-isopropylamino)propoxy]phenylpropionate hydrochloride which is substantially free of (R)-methyl-3-[4-(2-hydroxy-3-isopropylamino)propoxy]phenylpropionate hydrochloride ("S-Isomer in Table 1) to cause venous irritation in human patients. The rabbit was selected as the test system based upon established knowledge of its acceptability for use in vascular irritancy studies. Hessov and Bojen-Wøler, *Europ J Intens Care Med*, 2:97-101 (1976); Hessov et al., *Intens Care Med*, 5:79-81 (1979); Johnson et al., *J Oral Maxil Surg*, 47:819-822 (1989); Hoover et al., *Fundam Appl Toxicol*, 14:589-597 (1990). The rabbit model may be more sensitive than humans, but is nonetheless appropriate for demonstrating therapeutic concentrations which are likely to cause significant venous irritation in humans.

Ninety-six female, New Zealand White rabbits at a weight range of 2-3 kg were tested. The age of the rabbits was recorded at the time of testing. The rabbits were reportedly free of specified pathogens as determined by serology, bacteriology, and parasitology testing. Rabbits received water ad libitum, except during dosing, and Certified Hi-Fiber Rabbit LabDiet® (#5325) once daily. Water was periodically analyzed for microbial and chemical contaminants; no known contaminants in the feed or water were identified that would have interfered with this study.

The intravenous route of administration was selected because it is the intended route of administration in the clinical situation.

Prior to dosing, the hair around the marginal ear vein of both ears was clipped. The marginal vein of each ear was accessed using a 24 gauge intravascular catheter. The catheter was positioned so that the composition was administered in the direction of the blood flow. The calculated volume of the composition comprising the racemic mixture of methyl-3-[4-(2-hydroxy-3-isopropylamino)propoxy]phenylpropionate hydrochloride or (S)-methyl-3-[4-(2-hydroxy-3-isopropylamino)propoxy]phenylpropionate hydrochloride was administered in the left ear and the control composition (saline) was administered in the right ear by a pump programmed to deliver a volume that corresponds to a rate of 300 µg/kg/min. The injection sites on all animals were marked with indelible ink, or equivalent, for facile location at necropsy. The indelible ink was reapplied as needed.

Rabbits were separated into groups of four animals. Each animal from groups 1-12 received either an infusion of 5 mg/mL (i.e., 15 mM), 10 mg/mL (i.e., 30 mM), 20 mg/mL (i.e., 60 mM), 25 mg/mL (i.e., 75 mM), 35 mg/mL (i.e., 105 mM), or 50 mg/mL (i.e., 150 mM) of the racemic mixture of esmolol hydrochloride (RS) or the composition comprising the S-isomer of esmolol hydrochloride (S) into their marginal ear vein to compare irritation potential of the respective formulations, as indicated in Table 2. The ears of each rabbit were graded, according to the macroscopic findings classification presented in Table 3 approximately 2-4, 24, and 72 hours post-dosing.

TABLE 2

Study Design

| | Treatment | | Infusion Rate | Duration | Tissue Collection | |
|---|---|---|---|---|---|---|
| Group | Left Ear | Right Ear | (µg/kg/min) | (Hours) | 24 Hours | 72 Hours |
| 1 | R,S-Esmolol (5 mg/mL) | Saline Control | 300 | 4 | 1-4 | 5-8 |
| 2 | R,S-Esmolol (10 mg/mL) | Saline Control | 300 | 4 | 9-12 | 13-16 |
| 3 | R,S-Esmolol (20 mg/mL) | Saline Control | 300 | 4 | 17-20 | 21-24 |
| 4 | R,S-Esmolol (25 mg/mL) | Saline Control | 300 | 4 | 25-28 | 29-32 |
| 5 | R,S-Esmolol (35 mg/mL) | Saline Control | 300 | 4 | 33-36 | 37-40 |

TABLE 2-continued

Study Design

| | Treatment | | Infusion Rate | Duration | Tissue Collection | |
|---|---|---|---|---|---|---|
| Group | Left Ear | Right Ear | (μg/kg/min) | (Hours) | 24 Hours | 72 Hours |
| 6 | R,S-Esmolol (50 mg/mL) | Saline Control | 300 | 4 | 41-44 | 45-48 |
| 7 | S-Esmolol (5 mg/mL) | Saline Control | 300 | 4 | 49-52 | 53-56 |
| 8 | S-Esmolol (10 mg/mL) | Saline Control | 300 | 4 | 57-60 | 61-64 |
| 9 | S-Esmolol (20 mg/mL) | Saline Control | 300 | 4 | 65-68 | 69-72 |
| 10 | S-Esmolol (25 mg/mL) | Saline Control | 300 | 4 | 73-76 | 77-80 |
| 11 | S-Esmolol (35 mg/mL) | Saline Control | 300 | 4 | 81-84 | 85-88 |
| 12 | S-Esmolol (50 mg/mL) | Saline Control | 300 | 4 | 89-92 | 93-96 |
| 13 | S-Esmolol (88 mg/mL) | Saline Control | 300 | 4 | 1-4 | 5-8 |
| 14 | S-Esmolol (133 mg/mL) | Saline Control | 300 | 4 | 9-12 | 13-16 |

TABLE 3

Macroscopic Findings Classification

| Observations | Grade |
|---|---|
| Normal. No change other than that associated with injection trauma. | 0 |
| Slightly reddened/discolored. Redness or discoloration is limited to area of vein proximal to intravenous injection site note more than 25% of ear. | 1 (minimal) |
| Redness involving 25 to 100% of ear. | 2 (mild) |
| Deep red to purple discoloration. | 3 (moderate) |
| Pronounced purple discoloration. | 4 (severe) |

Tissue samples were collected approximately 24 or 72 hours after treatment, fixed in 10% neutral buffered formalin, trimmed, processed, embedded in paraffin, and sectioned. Hematoxylin-eosin stained slides were prepared and examined by light microscopy.

Three sections from each tissue sample (injection site) were evaluated. Five morphologic features were evaluated: endothelial loss, thrombosis, perivascular inflammation, perivascular edema, and perivascular hemorrhage. Endothelial loss was graded based on estimates of the relative circumference of the vein without endothelium. Thrombosis was graded based on the relative size of the thrombus and degree of vascular lumen obstruction. Perivascular inflammation and hemorrhage were graded based on the number and distribution of leukocytes and erythrocytes, respectively. The criteria for grading these features are detailed in Table 4.

TABLE 4

Criteria for Histopathologic Grading of Endothelial Loss, Thrombosis, Perivascular Inflammation, and Perivascular Hemorrhage

| | Endothelial Loss | Thrombosis | Inflammation and Hemorrhage |
|---|---|---|---|
| Grade 1 (Minimal) | <25% loss of endothelium | tags of fibrin | few scattered cells[a] or solitary focus |
| Grade 2 (Mild) | 25-75% loss of endothelium | thrombus with partial vascular lumen obstruction | multiple, focal collections of cells[a] |
| Grade 3 (Moderate) | <75% loss of endothelium | thrombus with complete or near complete vascular lumen obstruction | broad bands of cells[a] |

[a]Leukocytes for inflammation; erythrocytes for hemorrhage.

Perivascular edema was subjectively graded based on relative severity of the change: Grade 1=minimal, Grade 2=mild, Grade 3=moderate, Grade 4=marked.

Figure 1B:
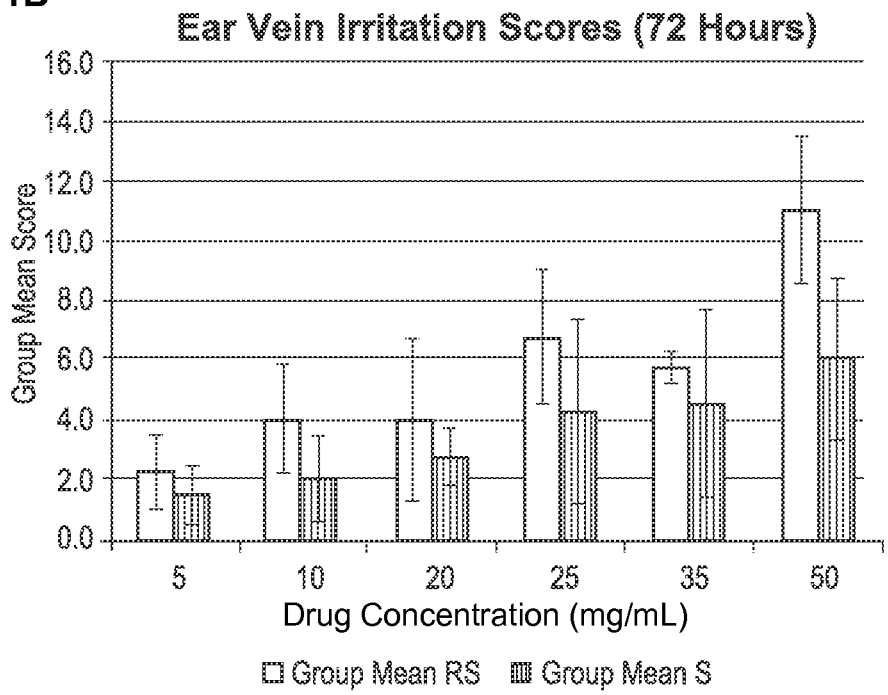
Figure 2A:
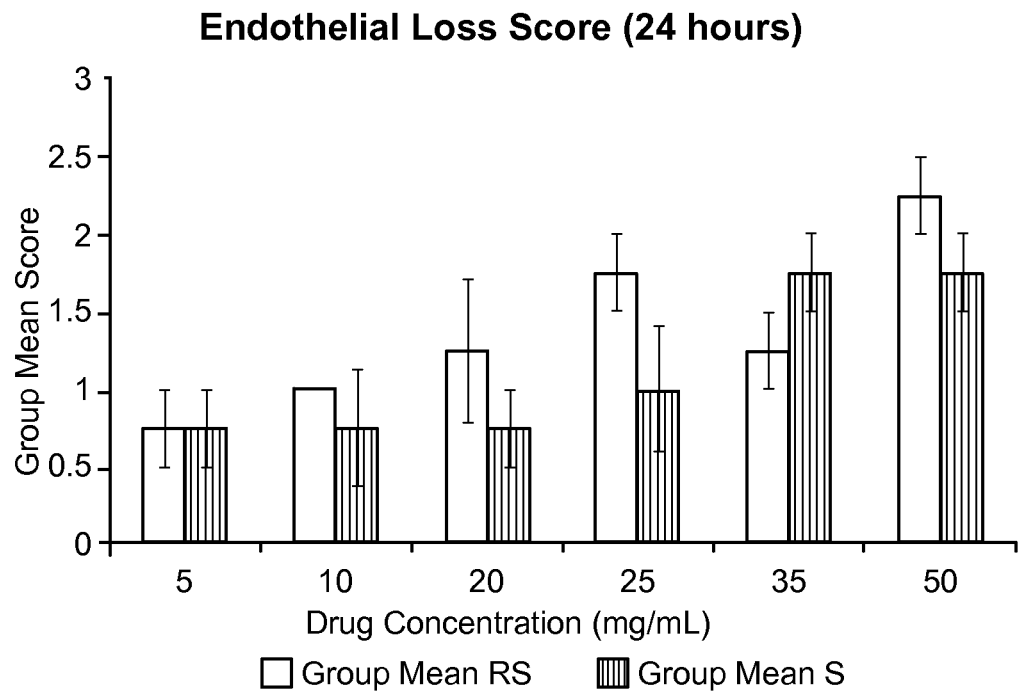
FIGS. 2A-2B illustrate the scores for the endothelial loss subcomponent of the rabbit ear vein irritation test comparing the effects of administering a composition comprising the racemic mixture of esmolol to a composition comprising the S-isomer of esmolol at 24 hours post-infusion (FIG. 2A) and 72 hours post-infusion (FIG. 2B).
Figure 2B:
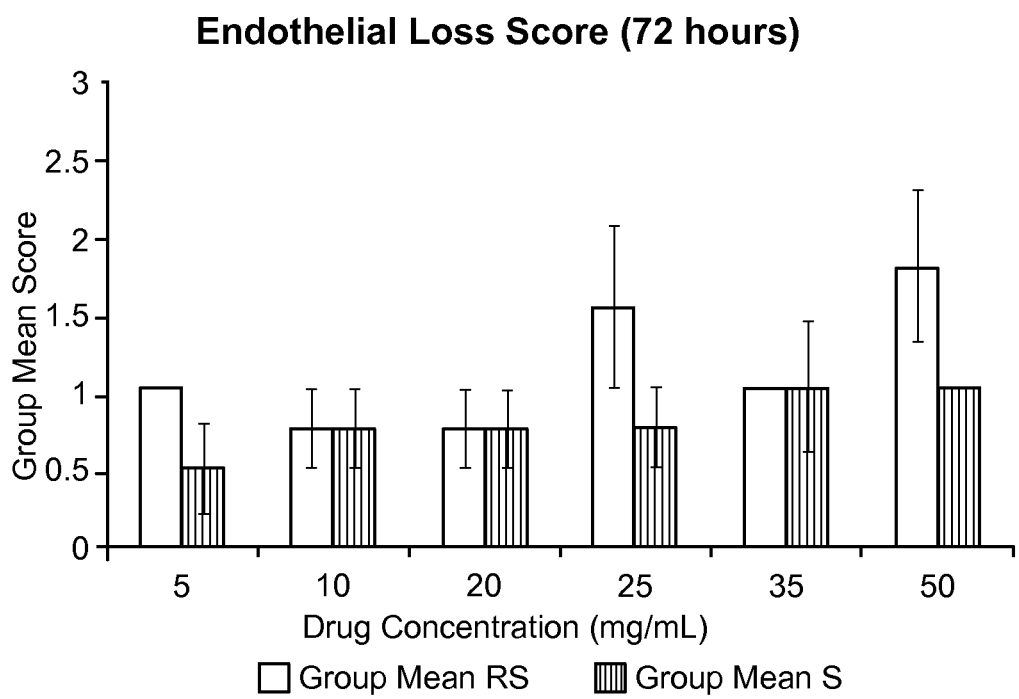
Figure 3A:
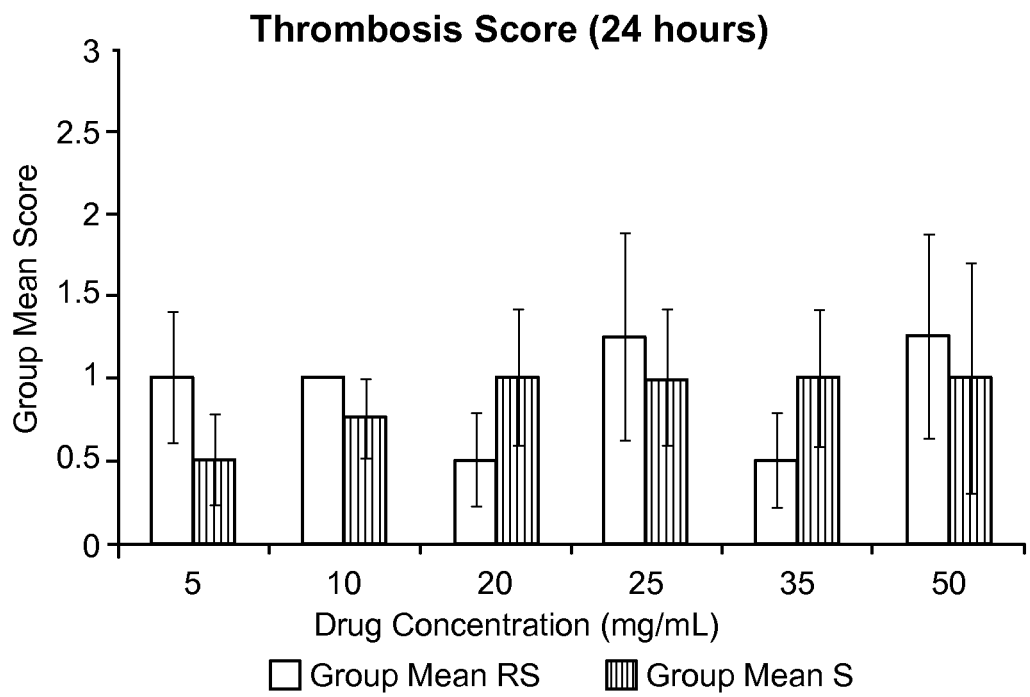
FIGS. 3A-3B illustrate the scores for the thrombosis subcomponent of the rabbit ear vein irritation test comparing the effects of administering a composition comprising the racemic mixture of esmolol to a composition comprising the S-isomer of esmolol at 24 hours post-infusion (FIG. 3A) and 72 hours post-infusion (FIG. 3B).
Figure 3B:
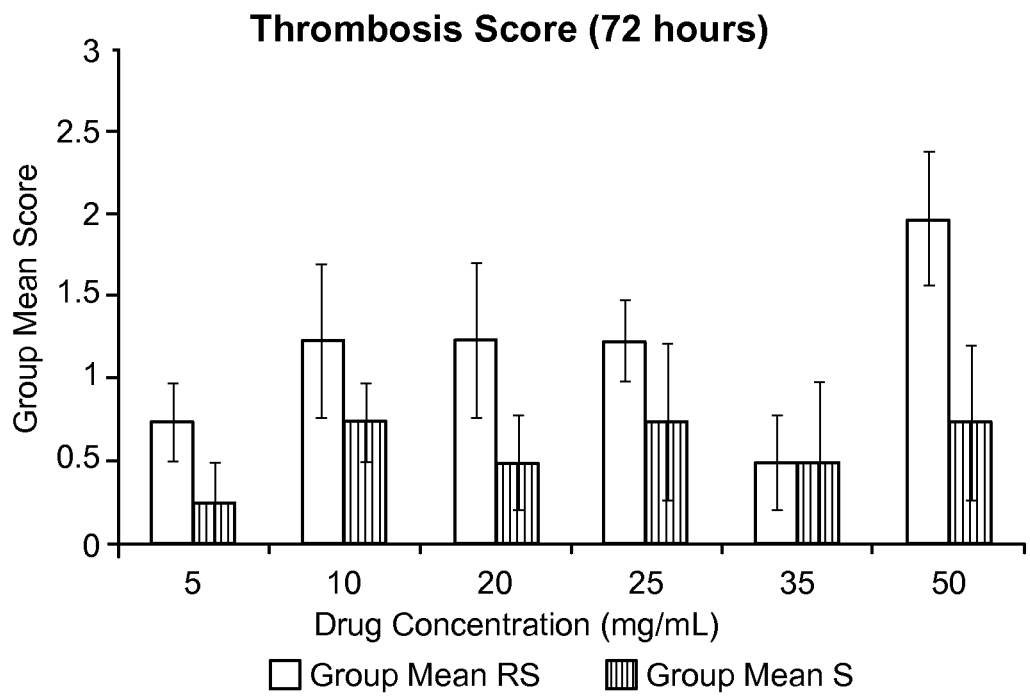
Figure 4A:
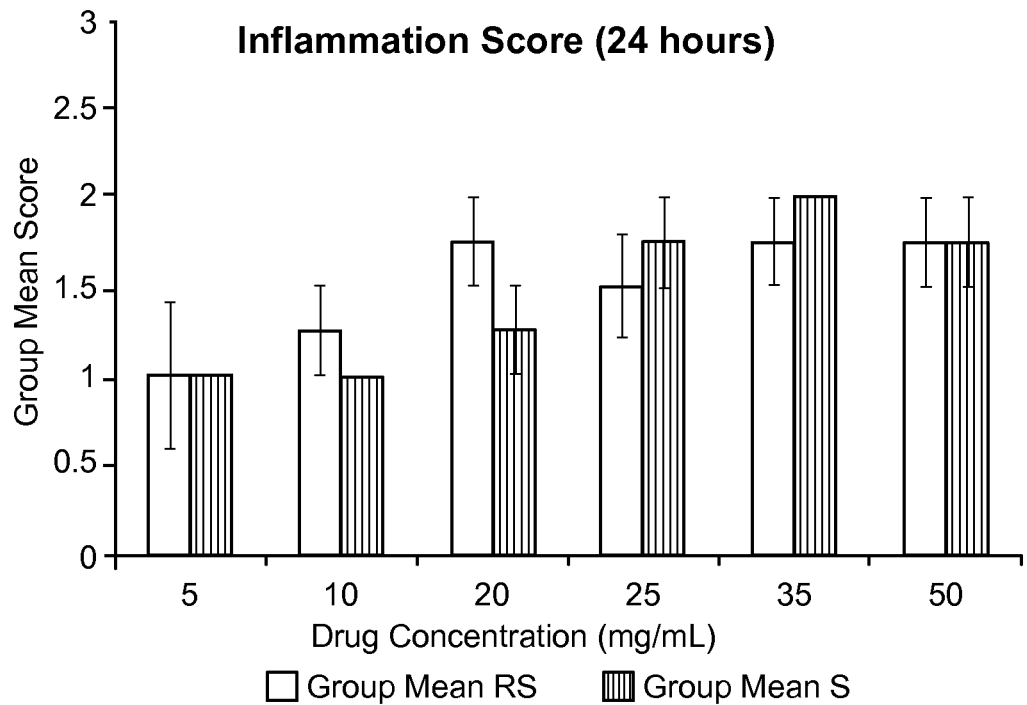
FIGS. 4A-4B illustrate the scores for the inflammation subcomponent of the rabbit ear vein irritation test comparing the effects of administering a composition comprising the racemic mixture of esmolol to a composition comprising the S-isomer of esmolol at 24 hours post-infusion (FIG. 4A) and 72 hours post-infusion (FIG. 4B).
Figure 4B:
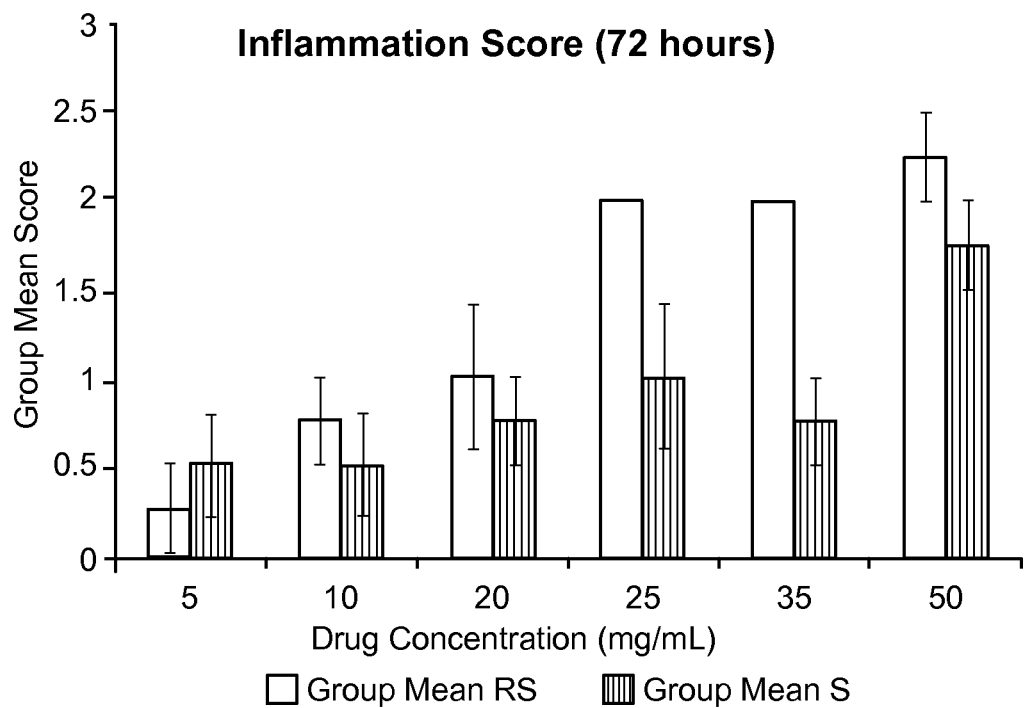
Figure 5A:
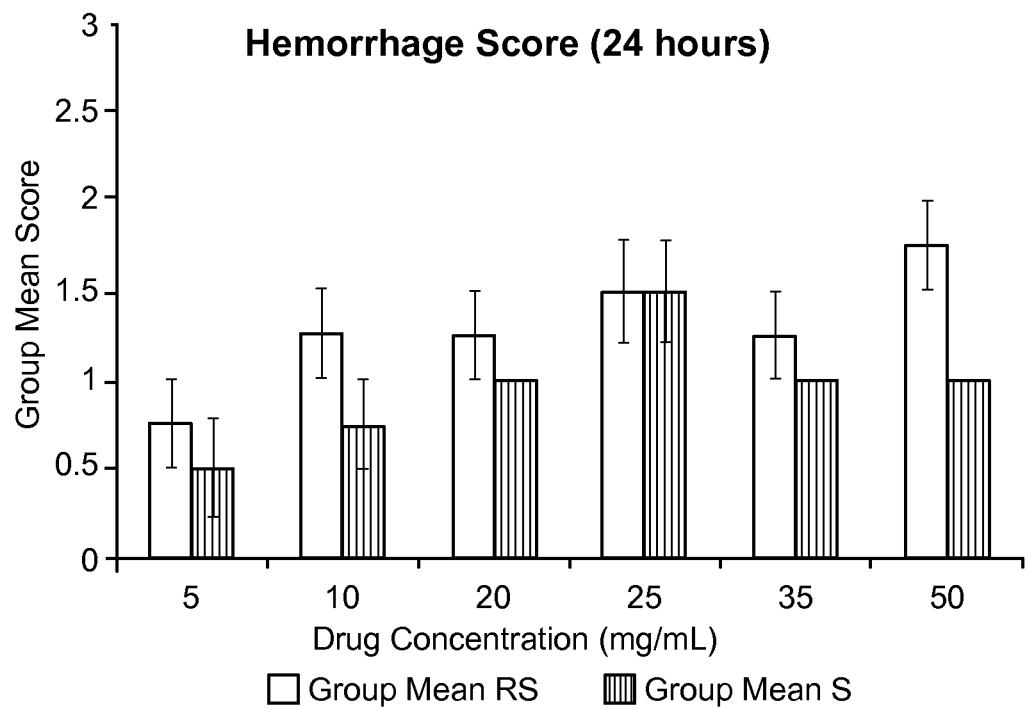
FIGS. 5A-5B illustrate the scores for the hemorrhage subcomponent of the rabbit ear vein irritation test comparing the effects of administering a composition comprising the racemic mixture of esmolol to a composition comprising the S-isomer of esmolol at 24 hours post-infusion (FIG. 5A) and 72 hours post-infusion (FIG. 5B).
Figure 5B:
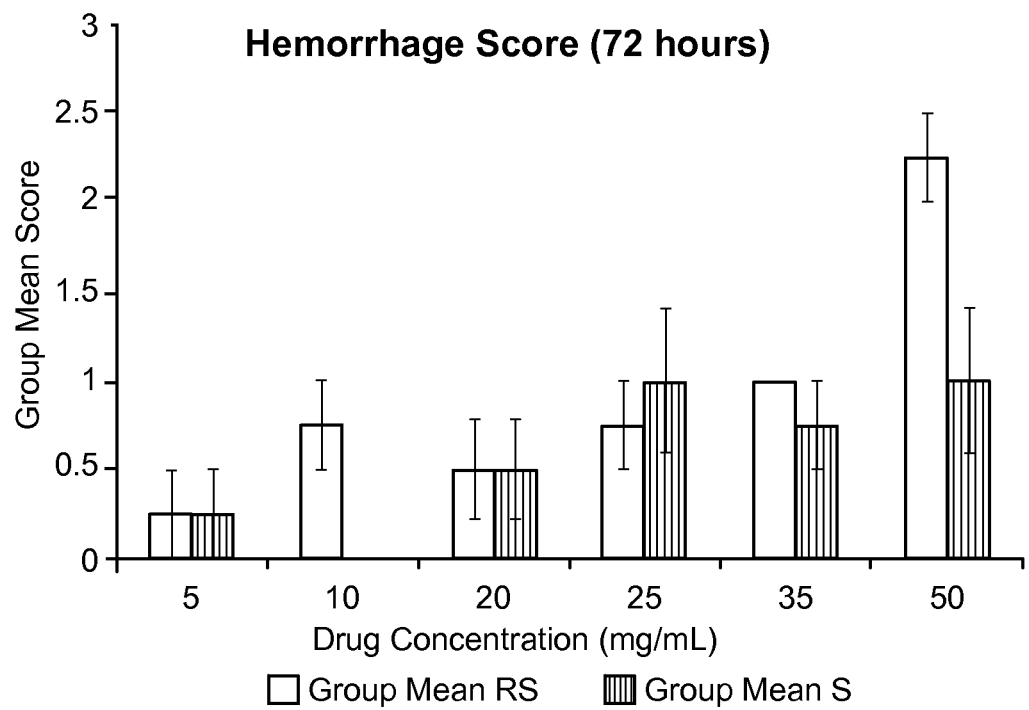
Figure 6A:
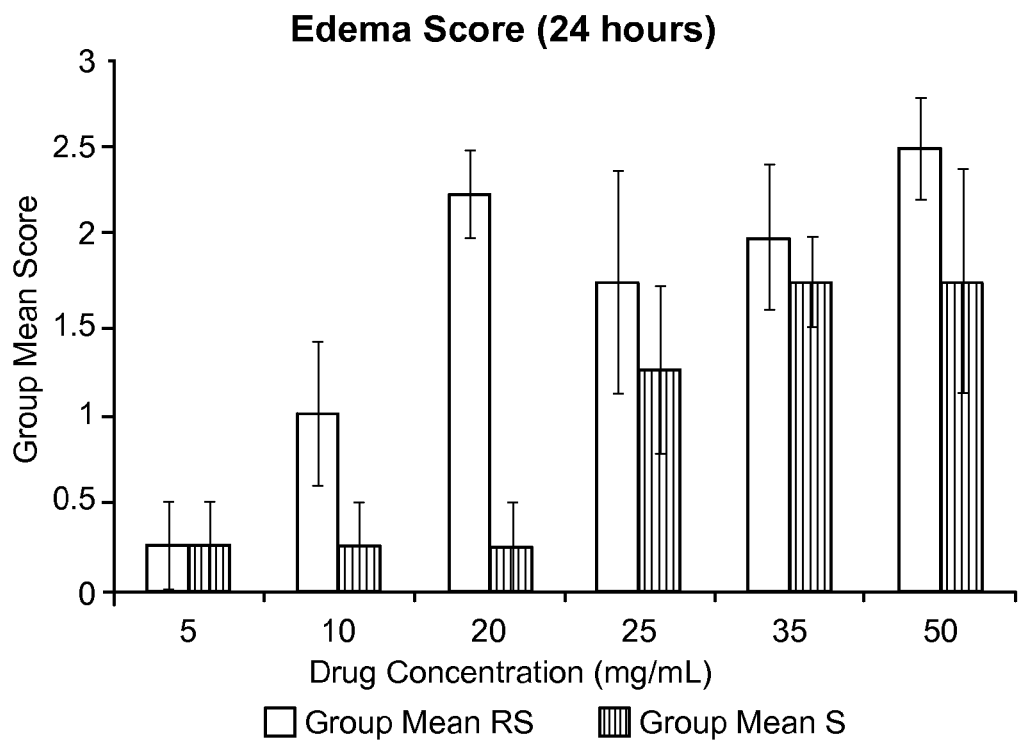
FIGS. 6A-6B illustrate the scores for the edema subcomponent of the rabbit ear vein irritation test comparing the effects of administering a composition comprising the racemic mixture of esmolol to a composition comprising the S-isomer of esmolol at 24 hours post-infusion (FIG. 6A) and 72 hours post-infusion (FIG. 6B).

Histopathologic observations of the site of infusion were made and scored at 24 hours post-infusion (FIG. 1a) and 72 hours post-infusion (FIG. 1b). FIG. 1 illustrates the total ear irritation composite score. This score is comprised of an endothelial loss score (FIG. 2), a thrombosis score (FIG. 3), an inflammation score (FIG. 4), a hemmorhage score (FIG. 5), and an edema score (FIG. 6).

Two-way analysis of variance (ANOVA) was performed at each time point using SAS® procedure MIXED. The dependent variables were each of the ear vein irritation scores for endothelial loss, thrombosis, inflammation, hemorrhage, edema, and their total scores (sum). Table 5 summarizes the statistical significance of comparing composite venous irritation test scores for the indicated concentrations of test compositions.

TABLE 5

| Comparison of Venous Irritation of Test Compositions on Basis of: | Time Point | All Composite Data of Venous-Irritation |
|---|---|---|
| Total Concentration (e.g., 20 mg/mL S vs. 20 mg/mL RS) | 24 h | Not significant |
| Total Concentration (e.g., 20 mg/mL S vs. 20 mg/mL RS) | 72 h | p = .002; ≥25 mg/mL |
| S-isomer Concentration (e.g., 10 mg/mL S vs. 20 mg/mL RS) | 24 h | p < .0001, all |
| S-isomer Concentration (e.g., 10 mg/mL S vs. 20 mg/mL RS) | 72 h | p = .0001, all |

At 24 hours post-infusion, rabbits receiving compositions comprising the racemic mixture R,S-esmolol hydrochloride at concentrations of ≥20 mg/mL (60 mM) had significantly higher irritation scores than those receiving concentrations ≤10 mg/mL R,S-esmolol hydrochloride (30 mM). At 24 hours post-infusion, rabbits receiving the composition comprising the S-isomer of esmolol hydrochloride which was substantially free of the R-isomer at concentrations of ≥25 mg/mL (75 mM) had significantly higher irritation scores than those receiving concentrations ≤20 mg/mL (60 mM) S-esmolol hydrochloride. The irritation scores for the racemic mixture and the S-isomer compositions began to diverge at esmolol hydrochloride concentrations of 20 mg/mL (60 mM), but concentrations ≥20 mg/mL (60 mM) did not cause significantly increased irritation at this early time point.

At 72 hours post-infusion, rabbits receiving compositions comprising the racemic mixture R,S-esmolol hydrochloride at concentrations of ≥25 mg/mL (75 mM) had significantly higher irritation scores than those receiving concentrations ≤20 mg/mL (60 mM) R,S-esmolol hydrochloride. At 72 hours post-infusion, rabbits receiving the composition comprising the S-isomer of esmolol hydrochloride which was substantially free of the R-isomer at concentrations of 50 mg/mL (150 mM) had significantly higher irritation scores than those receiving ≤35 mg/mL (105 mM) S-esmolol hydrochloride. The irritation scores began to diverge at esmolol hydrochloride concentrations of 25 mg/mL (75 mM). The racemic mixture of esmolol hydrochloride caused significantly greater irritation (p=0.002) at all concentrations ≥25 mg/mL (60 mM).

Because the S-isomer possesses substantially all of the therapeutic potential present in the racemic mixture, half the amount of S-isomer was considered equitherapeutic to a given amount of the racemic mixture of esmolol. Therefore, when a composition comprising 50 mg/mL (150 mM) of the racemic mixture of R,S-esmolol hydrochloride was administered, the equitherapeutic concentration of the S-isomer of esmolol hydrochloride which was administered for direct comparison was 25 mg/mL (75 mM). When comparing equitherapeutic concentrations (e.g., 50 mg/mL (150 mM) racemic mixture vs. 25 mg/mL (75 mM) S-isomer of esmolol) at 24 hours post-infusion, the irritation score was significantly higher (p<0.0001) for the compositions comprising the racemic mixture of esmolol at all concentrations tested.

Figure 6B:
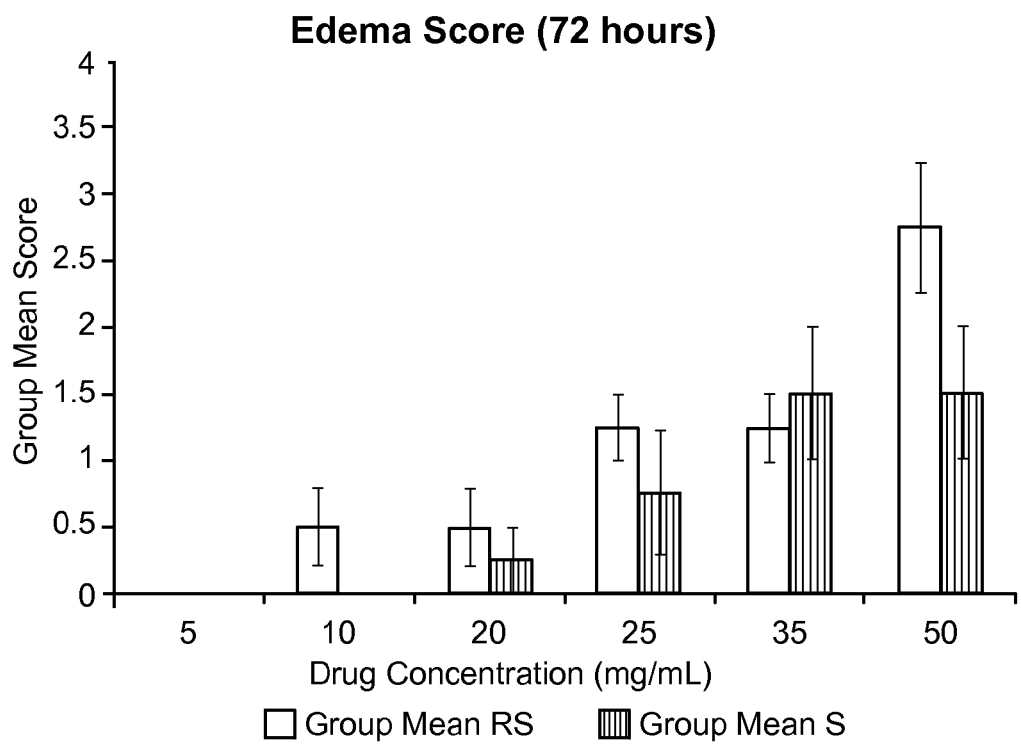

When comparing equitherapeutic concentrations at 72 hours post-infusion (e.g., 50 mg/mL (150 mM) of a composition comprising the racemic mixture vs. 25 mg/mL (75 mM) of a composition comprising the S-isomer of esmolol), the composite irritation score was significantly higher (p<0.0001) for the composition comprising the racemic mixture of esmolol at all concentrations tested (FIG. 1b). Similarly, when comparing equitherapeutic concentrations at 72 hours post-infusion, the composition comprising the racemic mixture of esmolol hydrochloride yielded scores that were significantly higher than the composition comprising the S-isomer of esmolol hydrochloride for every subcomponent of the rabbit ear vein irritation test. For endothelial loss, the p-value was 0.034 (FIG. 2b); for thrombosis, the p-value was 0.019 (FIG. 3b); for inflammation the p-value was <0.0001 (FIG. 4b); for hemorrhage the p-value was 0.001 (FIG. 5b); and for edema the p-value was <0.0001 (FIG. 6b).

Table 6 summarizes the statistical significance of comparing test scores for individual components of the venous irritation for the indicated concentrations of test compositions.

mixture, and that the effect of reduced venous irritation is particularly noticeable when the equitherapeutic concentration of the composition comprising the S-isomer of esmolol is compared to a corresponding concentration of the racemic mixture. These data further suggest that the R-isomer is contributing to the irritation potential of the racemic formulation.

Example 2

The study described in Example 1 was extended to assess the relative potential of (i) a composition comprising the racemic mixture of methyl-3-[4-(2-hydroxy-3-isopropylamino)propoxy]phenylpropionate hydrochloride ("Racemate" in Table 1) and (ii) compositions comprising 88 mg/mL or 133 mg/mL (S)-methyl-3-[4-(2-hydroxy-3-isopropylamino)propoxy]phenylpropionate hydrochloride which are substantially free of (R)-methyl-3-[4-(2-hydroxy-3-isopropylamino)propoxy]phenylpropionate hydrochloride ("S-Isomer in Table 1) to cause venous irritation in human patients.

Sixteen female, New Zealand White rabbits at a weight range of 2-3 kg and 15 weeks of age were tested. The rabbits were reportedly free of specified pathogens as determined by serology, bacteriology, and parasitology testing. Upon arrival, animals were quarantined for 7 days. Only rabbits showing no signs of clinical illness were used in this study. Animals were identified by an ear tag and housed individually in stainless-steel cages. Rabbits received water ad libitum, except during dosing, and Certified Hi-Fiber Rabbit Lab-Diet® (#5325) once daily. Rabbits were provided Timothy Hay Cubes or Nutra Blocks (Bio-Serv) 1-2 times per week. Water was periodically analyzed for microbial and chemical contaminants; no known contaminants in the feed or water were identified that would have interfered with this study.

S-isomer esmolol concentrations of 88 mg/mL and 133 mg/mL were evaluated in this study and represent concentrations 1.8 and 2.7 times higher than the highest concentration tested in Example 1. As in Example 1, a dosing rate of 300 μg/kg/min for 4 hours was used. The parameters of the study are shown in Table 2, groups 13 and 14.

Prior to dosing, the hair around the marginal ear vein of both ears was clipped. The marginal vein of each ear was accessed using a 24 gauge intravascular catheter. The catheter

TABLE 6

| Basis of Comparison | Time Point | All Data | Endothelial Cell Loss | Thrombosis | Inflammation | Hemorrhage | Edema |
|---|---|---|---|---|---|---|---|
| Total Concentration (20 mg/mL S vs. 20 mg/mL RS) | 24 h | | | | | | p = .003; ≥20 mg/mL |
| Total Concentration (20 mg/mL S vs. 20 mg/mL RS) | 72 h | p = .002; ≥25 mg/mL | p = .045; ≥25 mg/mL | | p = .0002; ≥25 mg/mL | | |
| S-isomer Concentration (10 mg/mL S vs. 20 mg/mL RS) | 24 h | p < .0001, all | p = .001, all | | p = .021; all | p = .003; all | p = .0001; all |
| S-isomer Concentration (10 mg/mL S vs. 20 mg/mL RS) | 72 h | p = .0001, all | p = .034, all | p = .019; all | p = .0001, all | p = .001: all | p = .0001; all |

Taken together, these data demonstrate our unexpected and surprising finding that significantly less venous irritation is observed when a composition comprising (S)-methyl-3-[4-(2-hydroxy-3-isopropylamino)propoxy]phenylpropionate or pharmaceutically acceptable salt thereof in an amount between 25 mg/mL (75 mM) and 50 mg/mL (150 mM) is administered relative to an equal concentration of the racemic was positioned so that the article is administered in the direction of the blood flow. The calculated volume of test article was administered in the left ear and the control article was administered in the right ear by a pump programmed to deliver a volume that corresponds to a rate of 300 μg/kg/min. The location of the injection site was marked with indelible ink at the time of injection.

One hour±10 minutes prior to dosing, rabbits were administered 0.03 mg/kg buprenorphine (an analgesic) subcutaneously. Additional buprenorphine doses were administered at approximately 8-12 hour intervals up to the 24 hour observation time point. At the 24 hour time point, the injection sites were evaluated to determine the gross irritation. If a grade 4 macroscopic irritation was observed in one or more animals in a group, the buprenorphine administration continued at 8-12 hour intervals until the 72 hour observation time point.

The ears of each rabbit were graded, according to the macroscopic findings classification presented in Table 3 approximately 2-4, 24, and 72 hours, as appropriate, post dosing.

On the day of termination and tissue collection, rabbits were anesthetized with up to 5% isoflurane in 1:2 oxygen: nitrous oxide, then euthanized with a sodium pentobarbital-containing solution administered by cardiac puncture. A full thickness section of the marginal ear vein and surrounding tissue (approximately 1.5 cm parallel to the long axis of the ear×1 cm perpendicular to the long axis of the ear) was excised from both the treated ear and the control ear of each rabbit. The section was excised beginning proximal to the catheter tip and the section was marked with a notch on the side closest to the catheter tip to orient the tissue for further histology processing. All sections were preserved in 10% neutral buffered formalin. Fixed samples were trimmed, processed, embedded in paraffin, and sectioned. Hematoxylin-eosin stained slides were prepared and examined by light microscopy.

Three sections from each tissue sample (injection site) were evaluated. Five morphologic features were evaluated: endothelial loss, thrombosis, perivascular inflammation, perivascular edema, and perivascular hemorrhage. Endothelial loss was graded based on estimates of the relative circumference of the vein without endothelium. Thrombosis was graded based on the relative size of the thrombus and degree of vascular lumen obstruction. Perivascular inflammation and hemorrhage were graded based on the number and distribution of leukocytes and erythrocytes, respectively. The criteria for grading these features are detailed in Table 4.

Perivascular edema was subjectively graded based on relative severity of the change: Grade 1=minimal, Grade 2=mild, Grade 3=moderate, Grade 4=marked.

The histologic section of each tissue sample (injection site) with the most severe change determined the grade for that morphologic feature in that sample. For each injection site, an overall score was derived by adding the observation grades for all observations. Morphologic features without positive observations were assigned Grade=0 to calculate an overall score. The degree of irritation was determined based upon macroscopic findings, in conjunction with microscopic findings. Findings for each test article group were compared to the corresponding control.

Individual macroscopic observations are summarized in Table 7. Scores for the test articles were higher relative to the saline controls. The summary of the results is shown in Table 8. The 88 mg/mL and 133 mg/mL S-isomer esmolol formulations exhibited moderate irritation and moderate to severe irritation, respectively, 24-72 hours after treatment. Tissue swelling was present at all S-isomer esmolol-treated injection sites.

TABLE 7

Individual Macroscopic and Histopathology Observations

| Description | Animal Number | Macroscopic Observations[a] | | | Histopathology Findings |
| | | Prior to Treatment | 2-4 Hr Post | 24 Hr Post | 72 Hr Post | |
|---|---|---|---|---|---|---|
| Group 1, 24 Hr Sacrifice | | | | | | |
| S-isomer, 88 mg/mL | 1 | 0 | $3^L$S | $3^L$S | — | Endothelial loss, moderate; Thrombosis, moderate; Inflammation, minimal; Hemorrhage, moderate; Edema, marked |
| | 2 | 0 | 3S | 3S | — | Endothelial loss, moderate; Thrombosis, mild; Inflammation, minimal; Hemorrhage, mild; Edema, marked |
| | 3 | 0 | 3S | 3S | — | Endothelial loss, moderate; Thrombosis, mild; Inflammation, minimal; Hemorrhage, mild; Edema, marked |
| | 4 | 0 | $3^L$S | $3^L$S | — | Endothelial loss, moderate; Thrombosis, moderate; Inflammation, minimal; Hemorrhage, moderate; Edema, marked |
| Saline | 1 | 0 | 0 | 0 | — | Thrombosis, minimal |
| | 2 | 0 | 0 | 0 | — | None |
| | 3 | 0 | 0 | 0 | — | Thrombosis, mild; Inflammation, minimal |
| | 4 | 0 | 0 | 0 | — | None |
| Group 1, 72 Hr Sacrifice | | | | | | |
| S-isomer, 88 mg/mL | 5 | 0 | 3S | 3S | $3^L$S | Endothelial loss, mild; Thrombosis, moderate; Inflammation, mild; Hemorrhage, mild; Edema, moderate |
| | 6 | 0 | 3S | 3S | $3^L$S | Endothelial loss, moderate; Thrombosis, moderate; Inflammation, mild; Hemorrhage, mild; Edema, marked |
| | 7 | 0 | $3^L$S | $3^L$S | 4 | Endothelial loss, moderate; Thrombosis, moderate; Inflammation, moderate; Hemorrhage, moderate; Edema, marked |
| | 8 | 0 | $3^L$S | $3^L$S | $3^L$S | Endothelial loss, moderate; Thrombosis, moderate; Inflammation, mild; Hemorrhage, moderate; Edema, marked |
| Saline | 5 | 0 | 0 | 0 | 0 | None |
| | 6 | 0 | 0 | 0 | 0 | None |
| | 7 | 0 | 0 | 0 | 0 | None |
| | 8 | 0 | 0 | 0 | 0 | None |
| Group 2, 24 Hr Sacrifice | | | | | | |
| S-isomer, 133 mg/mL | 9 | 0 | $3^L$S | $3^L$S | — | Endothelial loss, moderate; Thrombosis, moderate; Inflammation, mild; Hemorrhage, moderate; Edema, marked |
| | 10 | 0 | $3^L$S | $3^L$S | — | Endothelial loss, moderate; Thrombosis, moderate; Inflammation, mild; Hemorrhage, mild; Edema, marked |

TABLE 7-continued

Individual Macroscopic and Histopathology Observations

| | | Macroscopic Observations[a] | | | | |
|---|---|---|---|---|---|---|
| Description | Animal Number | Prior to Treatment | 2-4 Hr Post | 24 Hr Post | 72 Hr Post | Histopathology Findings |
| | 11 | 0 | 3[L]S | 3S | — | Endothelial loss, moderate; Thrombosis, moderate; Inflammation, mild; Hemorrhage, moderate; Edema, marked |
| | 12 | 0 | 3[L]S | 3[L]S | — | Endothelial loss, moderate; Thrombosis, moderate; Inflammation, mild; Hemorrhage, moderate; Edema, marked |
| Saline | 9 | 0 | 0 | 0 | — | None |
| | 10 | 0 | 0 | 0 | — | None |
| | 11 | 0 | 0 | 0 | — | Endothelial loss, minimal; Thrombosis, minimal |
| | 12 | 0 | 0 | 0 | — | None |
| | | | | | | Group 2, 72 Hr Sacrifice |
| S-isomer, 133 mg/mL | 13 | 0 | 3S | 3S | 3[L]S | Endothelial loss, moderate; Thrombosis, moderate; Inflammation, mild; Hemorrhage, moderate; Edema, marked |
| | 14 | 0 | 3[L]S | 3S | 3S | Endothelial loss, mild; Thrombosis, mild; Inflammation, moderate; Hemorrhage, mild; Edema, marked |
| | 15 | 0 | 3[L]S | 3S | 3S | Endothelial loss, moderate; Thrombosis, moderate; Inflammation, mild; Hemorrhage, moderate; Edema, moderate |
| | 16 | 0 | 4S | 4S | 4S | Endothelial loss, moderate; Thrombosis, moderate; Inflammation, moderate; Hemorrhage, moderate; Edema, marked |
| Saline | 13 | 0 | 0 | 0 | 0 | None |
| | 14 | 0 | 0 | 0 | 0 | None |
| | 15 | 0 | 1 | 0 | 0 | Endothelial loss, mild; Thrombosis, moderate |
| | 16 | 0 | 0 | 0 | 0 | None |

[a]Grade 0 = No grossly observable irritation.
Grade 1 - Slight Reddened/Discolored. Redness is limited to area of vein proximal to injection site (not more than 25% of the ear).
Grade 2 = Redness involving 25 to 100% of the ear.
Grade 3 = Deep red to purple discoloration
Grade 4 - Pronounced purple discoloration
S = Swelling
L = Discoloration limited to tissue adjacent to the vein
— = Not applicable, animals terminated prior to 72 hour time point

TABLE 8

Summary of Injection Site Overall Histologic Score for Test Specimens and Corresponding Saline Control, Intravenous Route

| | 24-hr Evaluation | | 72-hr Evaluation | |
|---|---|---|---|---|
| | Test | Control | Test | Control |
| S-isomer esmolol 88 mg/mL | 14 | 1 | 12 | 0 |
| | 12 | 0 | 14 | 0 |
| | 12 | 3 | 16 | 0 |
| | 14 | 0 | 15 | 0 |
| Group Mean | 13.0 | 1.0 | 14.3 | 0.0 |
| S-isomer esmolol 133 mg/mL | 15 | 0 | 15 | 0 |
| | 14 | 0 | 13 | 0 |
| | 15 | 2 | 14 | 5 |
| | 15 | 0 | 16 | 0 |
| Group Mean | 14.8 | 0.5 | 14.5 | 1.3 |

The mean overall scores for both concentrations of the S-isomer of esmolol were higher at both the 24-hour and 72-hour evaluations relative to the saline control specimens. Mean overall scores were similar at both formulation concentrations and approached the maximum possible irritation score of 16. Scores for 72-hour specimens were similar to scores for 24-hour specimens.

At the 24 hour evaluation of the 88 mg/mL concentration, histologic changes included moderate (Grade 3) endothelial loss, mild to moderate (Grades 2-3) thrombosis and perivascular hemorrhage, and marked (Grade 4) perivascular edema with minimal (Grade 1) perivascular inflammation. At the 133 mg/mL concentration, thrombosis was moderate (Grade 3) and perivascular inflammation was mild (Grade 2) in all specimens; otherwise, the severity of the histologic changes at 133 mg/mL was similar to the severity at the 88 mg/mL concentration.

At the 72 hour evaluation, the severity of histologic changes at the 88 mg/mL and 133 mg/mL concentrations were similar and included mild to moderate (Grades 2-3) endothelial loss, thrombosis, and perivascular hemorrhage and inflammation, and moderate to marked (Grades 3-4) perivascular edema.

Under the conditions of this study, histologic vascular irritation scores for specimens from rabbits given 88 mg/mL or 133 mg/mL formulations of the S-isomer of esmolol were similar at both concentrations and at both the 24-hour and 72-hour evaluations. Average irritation scores, 13.0-14.8, approached the maximum possible irritation score of 16. Taken together, these data demonstrate that the upper limit for the methods and compositions comprising (S)-methyl-3-[4-(2-hydroxy-3-isopropylamino)propoxy]phenylpropionate or pharmaceutically acceptable salt thereof that cause less venous irritation is about 50 mg/mL (corresponding to 150 mM).

What is claimed:

1. A pharmaceutical composition comprising: (S)-methyl-3-[4-(2-hydroxy-3-isopropylamino)propoxy]phenylpropionate or a pharmaceutically acceptable salt thereof, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof.

2. An aqueous pharmaceutical composition comprising: (S)-methyl-3-[4-(2-hydroxy-3-isopropylamino)propoxy]phenylpropionate or a pharmaceutically acceptable salt thereof, an osmotic adjusting agent, and a buffer, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof.

3. The aqueous pharmaceutical composition of claim 1, wherein the composition is substantially free of propylene glycol and ethanol.

4. The composition of claim 1, wherein the composition is ready-to use.

5. The composition of claim 1, wherein the composition is sterile.

6. The composition of claim 1, wherein the composition is suitable for parenteral infusion.

7. The composition of claim 1, wherein the composition has a pH of about 4.5 to about 5.5.

8. The composition of claim 1, wherein the composition comprises (S)-methyl-3-[4-(2-hydroxy-3-isopropylamino)propoxy]phenylpropionate hydrochloride at a concentration between about 20 mg/mL and about 50 mg/mL.

9. The composition of claim 1, wherein the composition comprises (S)-methyl-3-[4-(2-hydroxy-3-isopropylamino)propoxy]phenylpropionate or pharmaceutically acceptable salt thereof at a concentration between about 75 mM and about 150 mM.

10. The composition of claim 1, wherein the pharmaceutical composition contains less than 10% by weight by weight (R)-methyl-3-[4-(2-hydroxy-3-isopropylamino)propoxy]phenylpropionate or a pharmaceutically acceptable salt thereof based on the total amount of methyl-3-[4-(2-hydroxy-3-isopropylamino)propoxy]phenylpropionate or pharmaceutically acceptable salt thereof in the composition.

11. The composition of claim 1, wherein the pharmaceutical composition contains less than 5% by weight by weight (R)-methyl-3-[4-(2-hydroxy-3-isopropylamino)propoxy]phenylpropionate or a pharmaceutically acceptable salt thereof based on the total amount of methyl-3-[4-(2-hydroxy-3-isopropylamino)propoxy]phenylpropionate or pharmaceutically acceptable salt thereof in the composition.

12. The composition of claim 1, wherein the pharmaceutical composition contains less than 1% by weight by weight (R)-methyl-3-[4-(2-hydroxy-3-isopropylamino)propoxy]phenylpropionate or a pharmaceutically acceptable salt thereof based on the total amount of methyl-3-[4-(2-hydroxy-3-isopropylamino)propoxy]phenylpropionate or pharmaceutically acceptable salt thereof in the composition.

13. The composition of claim 9, wherein the pharmaceutical composition contains less than 5% by weight by weight (R)-methyl-3-[4-(2-hydroxy-3-isopropylamino)propoxy]phenylpropionate or a pharmaceutically acceptable salt thereof based on the total amount of methyl-3-[4-(2-hydroxy-3-isopropylamino)propoxy]phenylpropionate or pharmaceutically acceptable salt thereof in the composition.

14. The composition of claim 9, wherein the pharmaceutical composition contains less than 1% by weight by weight (R)-methyl-3-[4-(2-hydroxy-3-isopropylamino)propoxy]phenylpropionate or a pharmaceutically acceptable salt thereof based on the total amount of methyl-3-[4-(2-hydroxy-3-isopropylamino)propoxy]phenylpropionate or pharmaceutically acceptable salt thereof in the composition.

15. A method of treating a cardiac disorder comprising: administering to a subject in need thereof a therapeutically effective amount of a pharmaceutical composition comprising (S)-methyl-3-[4-(2-hydroxy-3-isopropylamino)propoxy]phenylpropionate or a pharmaceutically acceptable salt thereof, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof.

16. The method of claim 15, wherein the composition is substantially free of propylene glycol and ethanol.

17. The method of claim 15, wherein the cardiac condition is selected from the group consisting of tachycardia and hypertension.

18. The method of claim 17, wherein the tachycardia is selected from the group consisting of supraventricular tachycardia, intraoperative tachycardia and postoperative tachycardia.

19. The method of claim 15, wherein the subject is in need of fast control of severe tachyarrhythmia.

20. The method of claim 15, wherein the subject is on a salt-restricted diet.

21. The method of claim 15, wherein the subject is fluid restricted.

22. The method of claim 15, wherein the subject suffers from congestive heart failure.

23. The method of claim 15, wherein the subject is susceptible to venous irritation.

24. The method of claim 15, wherein the subject is concurrently taking a drug that is veno-irritative.

25. The method of claim 15, wherein the subject is suffering from an inflammatory condition selected from systemic lupus erythematosus and venous thrombosis.

26. The method of claim 15, wherein the subject is age 65 or older.

27. The method of claim 15, wherein the subject is diabetic.

28. The method of claim 15, wherein the subject is obese.

29. The method of claim 15, wherein the subject is an intravenous drug abuser.

30. The method of claim 15, wherein the composition comprises (S)-methyl-3-[4-(2-hydroxy-3-isopropylamino)propoxy]phenylpropionate hydrochloride at a concentration between about 20 mg/mL and about 50 mg/mL.

31. The method of claim 15, wherein the composition comprises (S)-methyl-3-[4-(2-hydroxy-3-isopropylamino)propoxy]phenylpropionate or pharmaceutically acceptable salt thereof at a concentration between about 75 mM and about 150 mM.

32. The method of claim 15, wherein the pharmaceutical composition contains less than 10% by weight or a pharmaceutically acceptable salt thereof based on the total amount of methyl-3-[4-(2-hydroxy-3-isopropylamino)propoxy]phenylpropionate or pharmaceutically acceptable salt thereof in the composition.

33. A method of controlling heart rate comprising: administering to a subject in need thereof a therapeutically effective amount of a pharmaceutical composition comprising (S)-methyl-3-[4-(2-hydroxy-3-isopropylamino)propoxy]phenylpropionate or a pharmaceutically acceptable salt thereof, wherein the (S)-methyl-3-[4-(2-hydroxy-3-isopropylamino)propoxy]phenylpropionate or pharmaceutically acceptable salt thereof is present at a concentration between about 60 mM and about 150 mM, and wherein the pharmaceutical composition is substantially free of (R)-methyl-3-[4-(2-hydroxy-3-isopropylamino)propoxy]phenylpropionate or pharmaceutically acceptable salt thereof.

34. The method of claim 33, wherein the composition is substantially free of propylene glycol and ethanol.

35. The method of claim 33, wherein the subject is on a salt-restricted diet.

36. The method of claim 33, wherein the subject is fluid restricted.

37. The method of claim 33, wherein the subject is susceptible to venous irritation.

38. The method of claim 33, wherein the subject is concurrently taking a drug that is veno-irritative.

39. The method of claim 33, wherein the subject is suffering from an inflammatory condition selected from systemic lupus erythematosus and venous thrombosis.

40. The method of claim 33, wherein the composition comprises (S)-methyl-3-[4-(2-hydroxy-3-isopropylamino)propoxy]phenylpropionate or pharmaceutically acceptable salt thereof at a concentration between about 75 mM and about 150 mM.

41. The method of claim 33, wherein the pharmaceutical composition contains less than 10% by weight (R)-methyl-3-[4-(2-hydroxy-3-isopropylamino)propoxy]phenylpropionate or a pharmaceutically acceptable salt thereof based on the total amount of methyl-3-[4-(2-hydroxy-3-isopropylamino)propoxy]phenylpropionate or pharmaceutically acceptable salt thereof in the composition.

* * * * *